United States Patent
Resconi et al.

(10) Patent No.: US 6,730,754 B2
(45) Date of Patent: May 4, 2004

(54) PROCESS FOR PRODUCING SUBSTANTIALLY AMORPHOUS PROPYLENE-BASED POLYMERS

(75) Inventors: Luigi Resconi, Ferrara (IT); Simona Guidotti, Casalecchio di Reno (IT); Giovanni Baruzzi, Ferrara (IT); Cristiano Grandini, Massafiscaglia (IT); Ilya E. Nifant'ev, Moscow (RU); Igor A. Kashulin, Moscow (RU); Pavel V. Ivchenko, Moscow (RU)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 09/936,832

(22) PCT Filed: Jan. 12, 2001

(86) PCT No.: PCT/EP01/00339

§ 371 (c)(1),
(2), (4) Date: Sep. 18, 2001

(87) PCT Pub. No.: WO01/53360

PCT Pub. Date: Jul. 26, 2001

(65) Prior Publication Data

US 2002/0147286 A1 Oct. 10, 2002

(30) Foreign Application Priority Data

Jan. 18, 2000 (EP) .............................. 00200193
Aug. 7, 2000 (EP) .............................. 00202791

(51) Int. Cl.[7] .................. C08F 4/44; C08F 110/06; C08F 210/06; B01J 31/38
(52) U.S. Cl. ................. 526/129; 526/161; 526/172; 526/351; 526/348; 526/348.6; 526/943; 502/117; 502/152; 502/155; 556/53
(58) Field of Search .................. 526/161, 172, 526/943, 351, 352, 129, 348, 348.6; 502/117, 155, 152; 556/53

(56) References Cited

U.S. PATENT DOCUMENTS 6,232,260 B1 * 5/2001 Nagy et al. ............. 502/155
6,559,251 B1   5/2003 Wang et al. ............. 526/127

FOREIGN PATENT DOCUMENTS

| | | | |
|---|---|---|---|
| EP | 0129368 | 12/1984 | C08F/10/00 |
| EP | 0416815 | 3/1991 | C07F/7/10 |
| EP | 0420436 | 4/1991 | C07F/7/00 |
| EP | 0575875 | 12/1993 | C08F/4/642 |
| EP | 0729984 | 9/1996 | C08F/210/16 |
| WO | 9602580 | 2/1996 | C08F/4/642 |
| WO | 9806727 | 2/1998 | C07F/17/00 |
| WO | 9806728 | 2/1998 | C07F/17/00 |
| WO | 9822486 | 5/1998 | C07F/17/00 |
| WO | 9837106 | 8/1998 | C08F/4/60 |
| WO | 9921899 | 5/1999 | C08F/10/02 |
| WO | 9924446 | 5/1999 | C07F/17/00 |
| WO | 9936427 | 7/1999 | C07F/17/00 |
| WO | 0075151 | 12/2000 | C07F/17/00 |
| WO | 0121674 | 3/2001 | C08F/10/00 |
| WO | 0147939 | 7/2001 | C07F/17/00 |
| WO | 0148039 | 7/2001 | C08F/10/02 |
| WO | 0148040 | 7/2001 | C08F/10/02 |

OTHER PUBLICATIONS

Ewen, J. A. et al., J. Am. Chem. Soc., 120: 10786–10787 (1998).

Resconi, Luigi et al., Chem. Rev., 100: 1253–1345 (2000).

* cited by examiner

Primary Examiner—Robert Deshon Harlan

(57) ABSTRACT

A process for producing substantially amorphous propylene (co)polymers, comprising contacting propylene optionally in the presence of one or more olefins under polymerization conditions with a catalyst system comprising: A) a half sandwich titanium complex wherein the cyclopentadienyl is substituted with one or two heterocyclic rings, according to formula (I): cf formula (I) in claim 1: wherein X is N or P; Z is C, Si or Ge; $Y^1$ is an atom selected from the group consisting of $NR^7$, O, $PR^7$ or S; $Y^2$ is selected from the group consisting of $CR^8$ or $Y^1$ and m is 0 or 1 and B) an activating cocatalyst. The above titanium complex and the ligand useful as intermediates in their synthesis are also described.

22 Claims, No Drawings

PROCESS FOR PRODUCING SUBSTANTIALLY AMORPHOUS PROPYLENE-BASED POLYMERS

This application is the U.S. national phase of International Application PCT/EP01/00339, filed Jan. 12, 2001.

The present invention relates to a new high yield process for producing substantially amorphous propylene-based polymers having high molecular weights. The invention also relates to the novel class of metal complexes used in the above-mentioned process, as well as to the ligands useful as intermediates in the synthesis of said metal complexes.

Metallocene compounds are well-known in the state of the art as catalyst components in olefin polymerization reactions, in association with suitable cocatalysts, such as alumoxanes or aluminum derivatives. For instance, EP 0 129 368 discloses a catalyst system for the polymerization of olefins comprising a bis-cyclopentadienyl coordination complex with a transition metal, wherein the two cyclopentadienyl groups may be linked by a divalent bridging group, such as an ethylene or a dimethylsilandiyl group.

Another class of polymerization catalysts known in the state of the art are the bridged cyclopentadienyl amido catalysts, which usually include monocyclopentadienyl titanium compounds activated by an alumoxane or other suitable cocatalysts (see for instance EP 0 416 815 and EP 0 420 436).

The international patent application WO 98/22486, in the name of the same Applicant, describes bridged and unbridged metallocenes comprising at least a coordinating group containing a six π electron central radical, directly coordinating a transition metal atom, to which are associated one or more radicals containing at least one non carbon atom selected from B, N, O, Al, Si, P, S, Ga, Ge, As, Se, In, Sn, Sb and Te. Said metallocenes are useful as catalyst components for the production of polyethylene and polypropylene.

The international patent application WO 98/37106 describes a polymerization catalyst system comprising a catalytic complex formed by activating a transition metal compound which comprises a group 13, 15 or 16 heterocyclic fused cyclopentadienide ligand and a metal selected from the group consisting of Group 3–9 and 10 metals; said heterocyclic fused cyclopentadienide ligand preferably contains, as endocyclic heteroatoms, one or more B, N, P, O, or S atoms.

The international patent application WO 99/24446, in the name of the same Applicant, describes bridged and unbridged metallocenes comprising at least a heterocyclic cyclopentadienyl group of one of the following formulae:

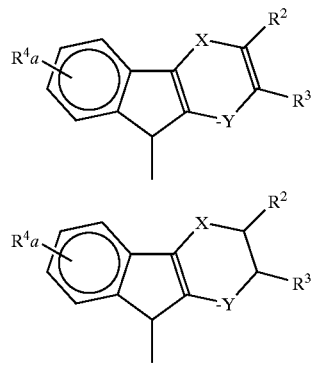

wherein one of X or Y is a single bond, the other being O, S, NR or PR, R being hydrogen or an hydrocarbon group;

$R^2$, $R^3$ and $R^4$ are hydrogen, halogen, —R, —OR, —OCOR, —SR, —NR$_2$ or —PR$_2$; a is 0–4. These metallocenes may be used as catalyst components in the polymerization of olefins, particularly in the production of homo and copolymers of ethylene.

The international applications WO 98/06727 and WO 98/06728 describe respectively 3-heteroatom and 2-heteroatom substituted cyclopentadienyl-containing metal complexes, useful as catalysts for olefin polymerization; more specifically, these complexes contain a heteroatom-Cp bond, respectively in the 3-position and 2-position of the Cp, and are used for preparing ethylene/1-octene copolymers.

The Applicant has now unexpectedly found a new class of metallocene compounds useful as catalyst components in propylene polymerization, able to produce high molecular weight substantially amorphous propylene (co)polymers in high yields.

An object of the present invention is a process for producing substantially amorphous propylene homopolymers or copolymers comprising contacting propylene, optionally in the presence of one or more olefins selected from the group consisting of ethylene, alpha-olefins of formula CH$_2$=CHR' wherein R' is a linear or branched C$_2$–C$_{10}$ alkyl or non conjugate diolefins containing up to 20 carbon atoms, under polymerization conditions with a catalyst system comprising:

A) a titanium complex of formula (I):

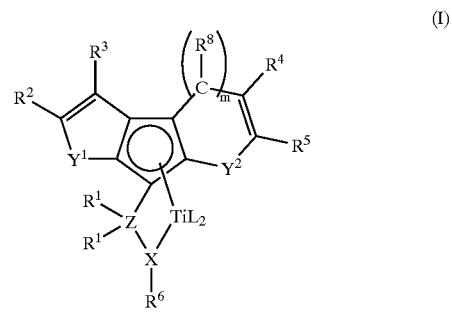

wherein: Ti is titanium;

X is a nitrogen or phosphorus atom;

Z is a C, Si or Ge atom; the groups R$^1$, equal to or different from each other, are selected from the group consisting of hydrogen, linear or branched, saturated or unsaturated C$_1$–C$_{20}$ alkyl, C$_3$–C$_{20}$ cycloalkyl, C$_6$–C$_{20}$ aryl, C$_7$–C$_{20}$ alkylaryl and C$_7$–C$_{20}$ arylalkyl radicals optionally containing Si or heteroatoms belonging to groups 13 or 15–17 of the Periodic Table of the Elements, or two R$^1$ groups form together a C$_4$–C$_7$ ring;

Y$^1$ is an atom selected from the group consisting of NR$^7$, oxygen (O), PR$^7$ or sulfur (S), wherein the group R$^7$ is selected from the group consisting of linear or branched, saturated or unsaturated, C$_1$–C$_{20}$ alkyl, C$_6$–C$_{20}$ aryl and C$_7$–C$_{20}$ arylalkyl radical;

the groups R$^2$ and R$^3$, equal to or different from each other, are selected from the group consisting of hydrogen, halogen, —R, —OR, —OCOR, —OSO$_2$CF$_3$, —SR, —NR$_2$ and —PR$_2$, wherein R is a linear or branched, saturated or unsaturated C$_1$–C$_{20}$ alkyl, C$_3$–C$_{20}$ cycloalkyl, C$_6$–C$_{20}$ aryl, C$_7$–C$_{20}$ alkylaryl or C$_7$–C$_{20}$ arylalkyl radical; two R can also form a saturated or unsaturated C$_4$–C$_7$ ring, preferably R is methyl, ethyl, n-propyl, isopropyl, n-butyl, t-butyl, phenyl, p-n-butyl-phenyl or benzyl radical, or R$^2$ and R$^3$ form a condensed aromatic or aliphatic C$_4$–C$_7$ ring that can be substituted with one or more $R^9$ groups wherein $R^9$ is selected from the group consisting of halogen, —R, —OR, —OCOR, —OSO$_2$CF$_3$, —SR, —NR$_2$ and —PR$_2$, wherein R has the meaning reported above, or two vicinal $R^9$ groups form together a condensed aromatic or aliphatic $C_4$–$C_7$ ring;

the groups $R^8$, $R^4$ and $R^5$, equal to or different from each other, are selected from the group consisting of hydrogen, halogen, —R, —OR, —OCOR, —OSO$_2$CF$_3$, —SR, —NR$_2$ and —PR$_2$, wherein R has the meaning reported above, or $R^8$ and $R^4$, $R^4$ and $R^5$ or $R^5$ and $R^8$ form together a condensed $C_4$–$C_7$ ring that optionally can be substituted with one or more R groups;

the group $R^6$ is selected from the group consisting of a linear or branched, saturated or unsaturated $C_1$–$C_{20}$ allyl, $C_6$–$C_{20}$ aryl and $C_7$–$C_{20}$ arylalkyl radical, optionally containing heteroatoms belonging to groups 13 or 15–17 of the Periodic Table of the Elements;

the substituents L, equal to or different from each other, are monoanionic sigma ligands selected from the group consisting of hydrogen, halogen, —R, —OR, —OCOR, —OSO$_2$CF$_3$, —SR, —NR$_2$ and —PR$_2$, wherein R has the meaning reported above;

$Y^2$ is selected from the group consisting of $CR^8$ or $Y^1$; and m is 0 or 1; when the group $Y^2$ is a $CR^8$ group m is 1 and the 6 membered ring formed is an aromatic benzene ring, when $Y^2$ is different from $CR^8$ m is 0 and the carbon atom bonding the $R^4$ group is directly bonded to the cyclopentadienyl ring and the ring formed is a 5 membered ring; i.e. when m is 1 the compound of formula (I) has the following formula (Ia);

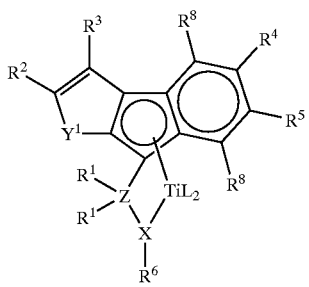

(Ia)

and when m is 0 the compound of formula (I) has the following formula (Ib);

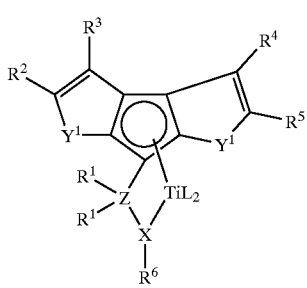

(Ib)

wherein L, X, Z, $Y^1$, m, $R^1$, $R^2$, $R^3$, $R^4$, $R^5$, $R^6$ and $R^8$ have the meaning reported above; and (B) an activating cocatalyst.

The present invention further concerns a titanium complex of formula (I), as reported above, as well as the corresponding ligand of formula (II):

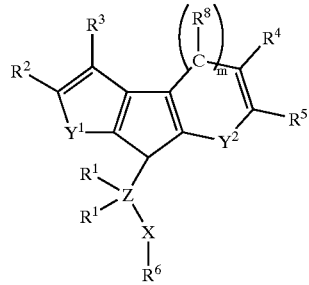

(II)

wherein X, Z, $Y^1$, m, $R^1$, $R^2$, $R^3$, $R^4$, $R^5$, $R^6$ and $R^8$ have the meaning reported above; the above ligands are particularly useful as intermediates in the preparation of the titanium complexes of formula (I), according to the invention.

The titanium complex of formula (I) may be suitably used according to the present invention in a complexed form, for example in the presence of a coordination molecules such as Lewis bases. Preferred complexes of formula (I) are those belonging to the following three classes (1), (2) and (3), having respectively formula (III), (IV) and (V).

Class (1)

Titanium complexes belonging to class (1) have the following formula (III)

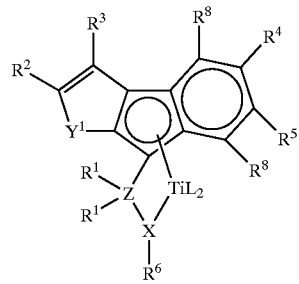

(III)

wherein X, Z, $Y^1$, L, $R^1$, $R^2$, $R^3$, $R^4$, $R^5$, $R^6$ and $R^8$ have the meaning reported above with the proviso that $R^2$ and $R^3$ do not form a condensed aromatic or aliphatic $C_4$–$C_7$ ring.

Preferably in the titanium complexes of formula (III):

X is a nitrogen atom; the divalent bridge >ZR$^1$$_2$ is preferably selected from the group consisting of dimethylsilyl, diphenylsilyl, diethylsilyl, di-n-propylsilyl, di-isopropylsilyl, di-n-butyl-silyl, di-t-butyl-silyl, di-n-hexylsilyl, ethylmethylsilyl, n-hexylmethylsilyl, cyclopentamethylenesilyl, cyclotetramethylenesilyl, cyclotrimethylenesilyl, methylene, dimethylmethylene and diethylmethylene; even more preferably, it is dimethylsilyl, diphenylsilyl or dimethylmethylene;

$Y^1$ is N-methyl, N-ethyl or N-phenyl;

$R^2$ and $R^3$, equal to or different from each other, are selected from the group consisting of hydrogen, halogen, —R, —OR, —OCOR, —OSO$_2$CF$_3$, —SR, —NR$_2$ and —PR$_2$; more preferably $R^2$ is hydrogen methyl, ethyl, propyl or phenyl; and $R^3$ is hydrogen methyl or phenyl; even more preferably $R^2$ is hydrogen or methyl;

$R^4$ and $R^8$ are hydrogen;

$R^5$ is hydrogen, methoxy or tertbutyl;

$R^6$ is selected from the group consisting of methyl, ethyl, n-propyl, isopropyl, n-butyl, t-butyl, phenyl, p-n-butyl-phenyl, benzyl, cyclohexyl and cyclododecyl; more preferably $R^6$ is t-butyl; the substituents L, equal to or different from each other, are preferably halogen atoms, linear or branched, saturated or unsaturated $C_7$–$C_{20}$ alkylaryl, $C_1$–$C_6$ alkyl groups or OR wherein R is described above; more preferably the substituents L are Cl, $CH_2C_6H_5$, $OCH_3$ or $CH_3$.

Non limiting examples of complexes of formula (III) are:

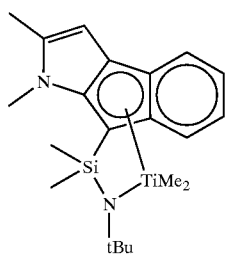
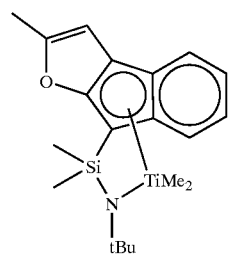
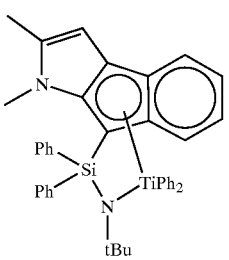
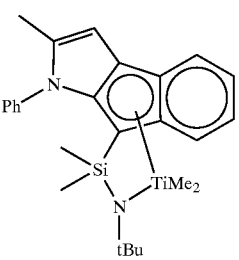

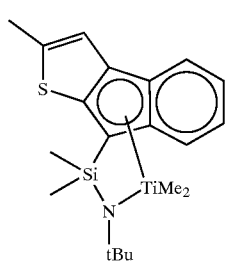
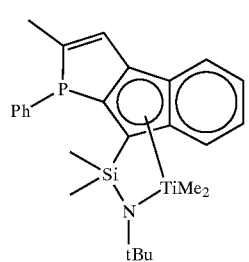
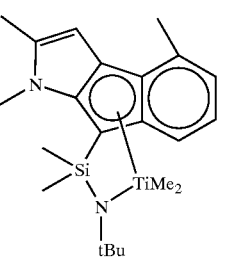
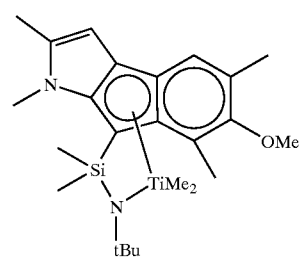

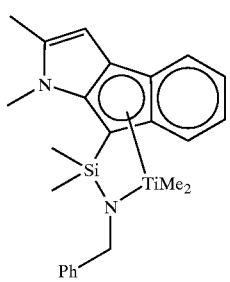
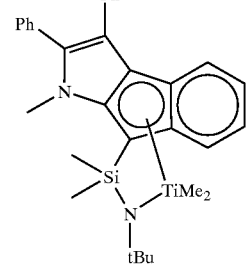
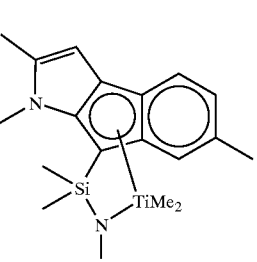
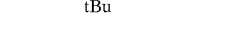

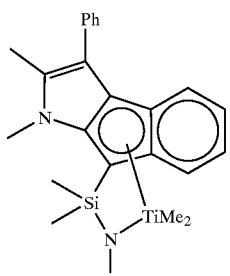
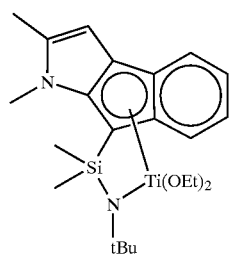

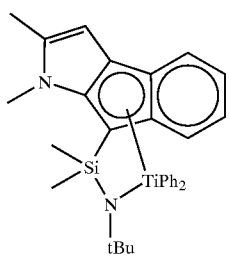
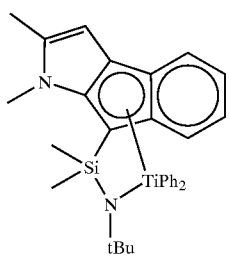

and the corresponding titanium dichloride or dimethoxy complexes.

The titanium complexes belonging to class (1) can be prepared starting from the ligand of formula (IIIa)

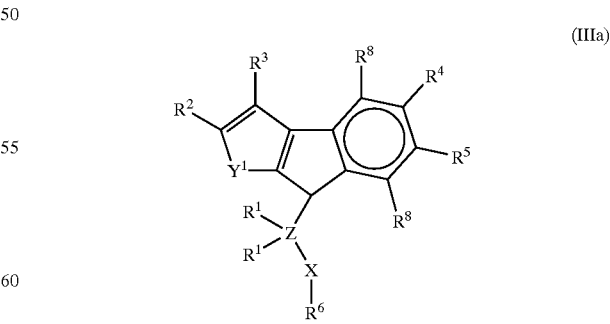

(IIIa)

wherein X, Z, $Y^1$, $R^1$, $R^2$, $R^3$, $R^4$, $R^5$, $R^6$ and $R^8$ have the meaning reported above.

Class (2)

Titanium complexes of class (2) have the following formula (IV)

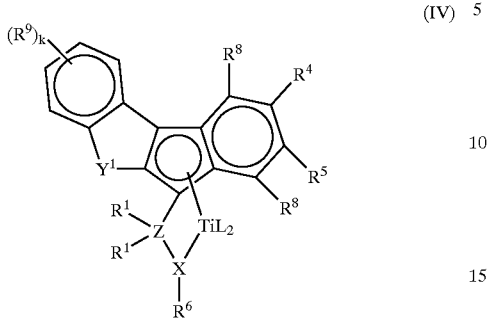

wherein X, Z, $Y^1$, L, $R^1$, $R^4$, $R^5$, $R^6$, $R^8$, and $R^9$ have the meaning reported above and k ranges from 0 to 4.

Preferably in the titanium complexes of formula (IV):

X is a nitrogen atom; the divalent bridge >$ZR^1_2$ is selected from the group consisting of dimethylsilyl, diphenylsilyl, diethylsilyl, di-n-propylsilyl, di-isopropylsilyl, di-n-butyl-silyl, di-t-butyl-silyl, di-n-hexylsilyl, ethylmethylsilyl, n-hexylmethylsilyl, cyclopentamethylenesilyl, cyclotetramethylenesilyl, cyclotrimethylenesilyl, methylene, dimethylmethylene and diethylmethylene; even more preferably, it is dimethylsilyl, diphenylsilyl or dimethylmethylene;

$Y^1$ is N-methyl, N-ethyl or N-phenyl;

k is 0 or 1 and $R^9$ is 2-methyl, 2-isopropyl and 2-tert-butyl;

$R^6$ is selected from the group consisting of methyl, ethyl, n-propyl, isopropyl, n-butyl, t-butyl, phenyl, p-n-butyl-phenyl, benzyl, cyclohexyl and cyclododecyl; more preferably $R^6$ is t-butyl;

$R^4$, $R^5$ and $R^8$ are hydrogen atoms;

the substituents L, equal to or different from each other, are halogen atoms, linear or branched, saturated or unsaturated $C_1$–$C_6$ alkyl, $C_7$–$C_{20}$ alkylaryl groups or OR wherein R is defined above;

more preferably the substituents L are Cl, $CH_3$, $OCH_3$ or $CH_2C_6H_5$.

Non limiting examples of titanium complexes of formula (IV), according to the present invention, are the following:

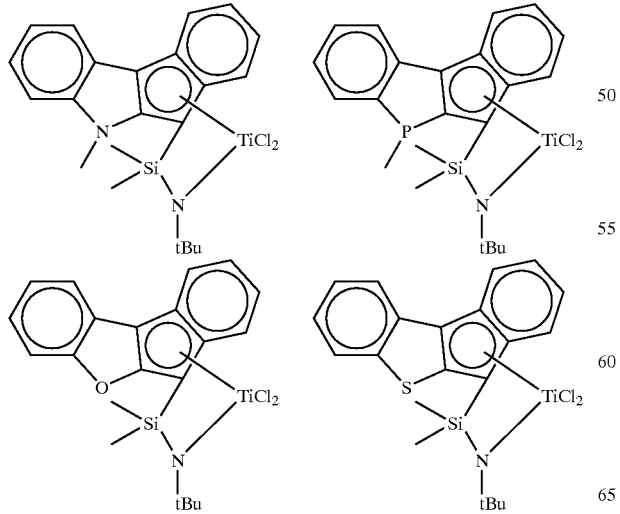

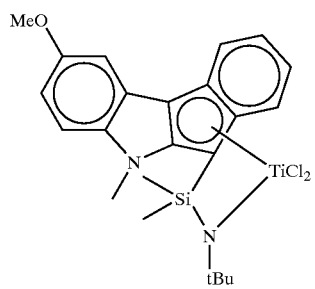

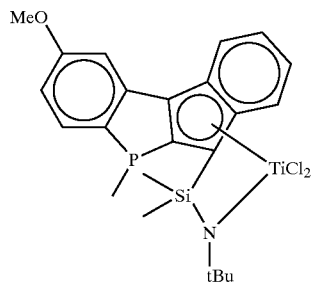

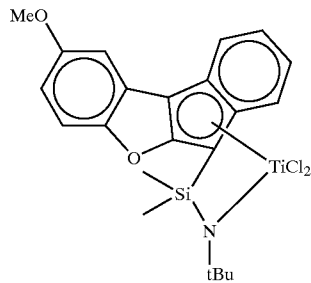

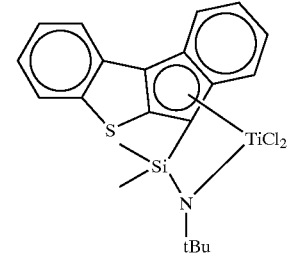

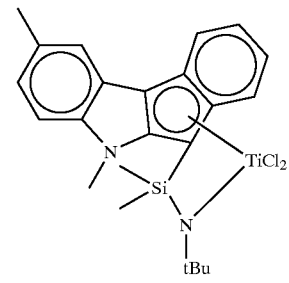

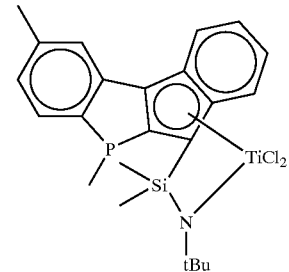

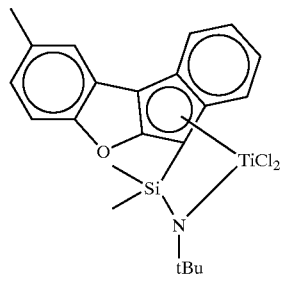
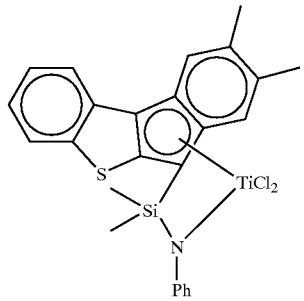
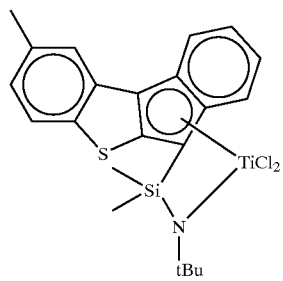
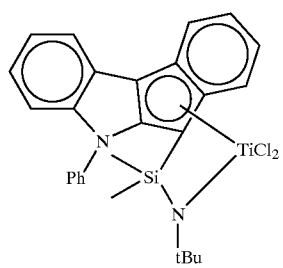
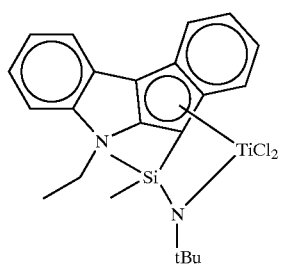
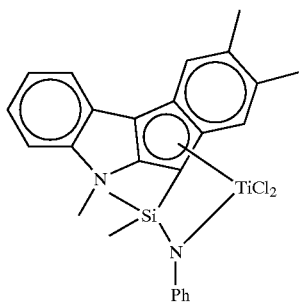
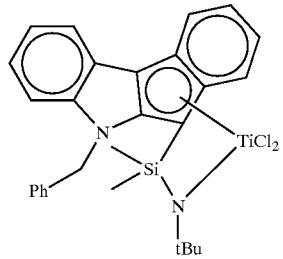
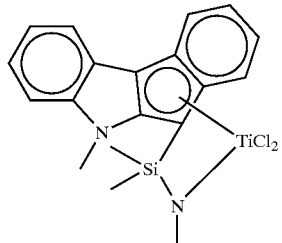
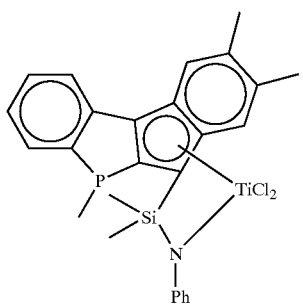
and the corresponding titanium dimethyl or dimethoxy complexes.
The titanium complexes belonging to class (2) can be prepared starting from the ligand of formula (IVa)
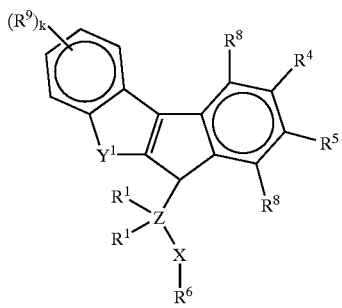
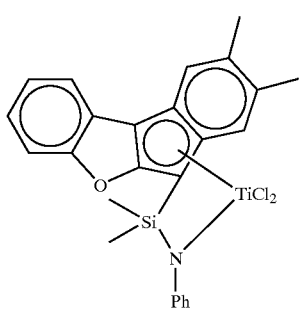
wherein X, Z, $Y^1$, $R^1$, $R^4$, $R^5$, $R^6$, $R^8$, $R^9$ and k have the meaning reported above.

Class (3)

Titanium complexes belonging to class (3) have the following formula (V):

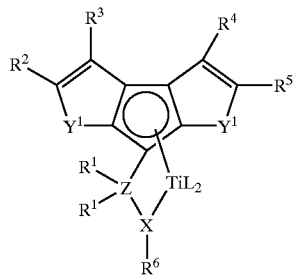

wherein X, Z, L, $Y^1$, $R^1$, $R^2$, $R^3$, $R^4$, $R^5$ and $R^6$ have the meaning reported above.

Preferably in the titanium complexes of formula (IV):

X is a nitrogen atom; the divalent bridge $>ZR^1_2$ is preferably selected from the group consisting of dimethylsilyl, diphenylsilyl, diethylsilyl, di-n-propylsilyl, di-isopropylsilyl, di-n-butyl-silyl, di-t-butyl-silyl, di-n-hexylsilyl, ethylmethylsilyl, n-hexylmethylsilyl, cyclopentamethylenesilyl, cyclotetramethylenesilyl, cyclotrimethylenesilyl, methylene, dimethylmethylene and diethylmethylene; even more preferably, it is dimethylsilyl, diphenylsilyl or dimethylmethylene;

two $Y^1$ are the same group; more preferably they are $NR^7$ or S;

$R^2$ is hydrogen, methyl, ethyl, propyl or phenyl; and $R^3$ is hydrogen or $R^2$ and $R^3$ form a condensed benzene ring that can be substituted with one or more R groups;

$R^4$ is hydrogen and $R^5$ is hydrogen methyl, ethyl, propyl or phenyl or $R^4$ and $R^5$ form a condensed benzene ring that can be substituted with one or more R groups;

$R^6$ is preferably selected from the group consisting of methyl, ethyl, n-propyl, isopropyl, n-butyl, t-butyl, phenyl, p-n-butyl-phenyl, benzyl, cyclohexyl and cyclododecyl; more preferably $R^6$ is t-butyl;

the substituents L, equal to or different from each other, are preferably halogen atoms linear or branched, saturated or unsaturated $C_7$–$C_{20}$ alkylaryl, $C_1$–$C_6$ alkyl groups or OR; more preferably the substituents L are Cl, $CH_2C_6H_5$, $OCH_3$ or $CH_3$.

Non limiting examples of complex of formula (IV) are:

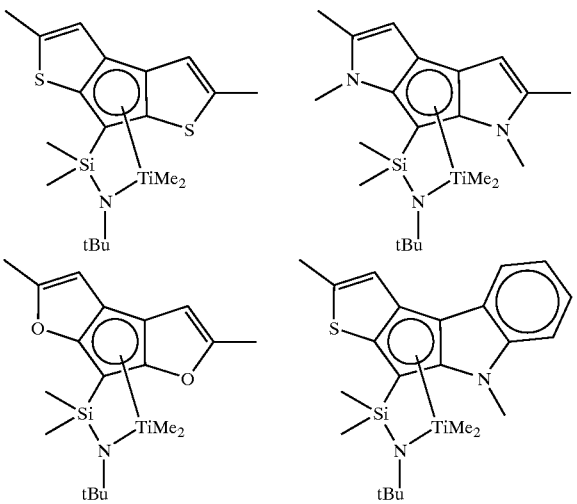

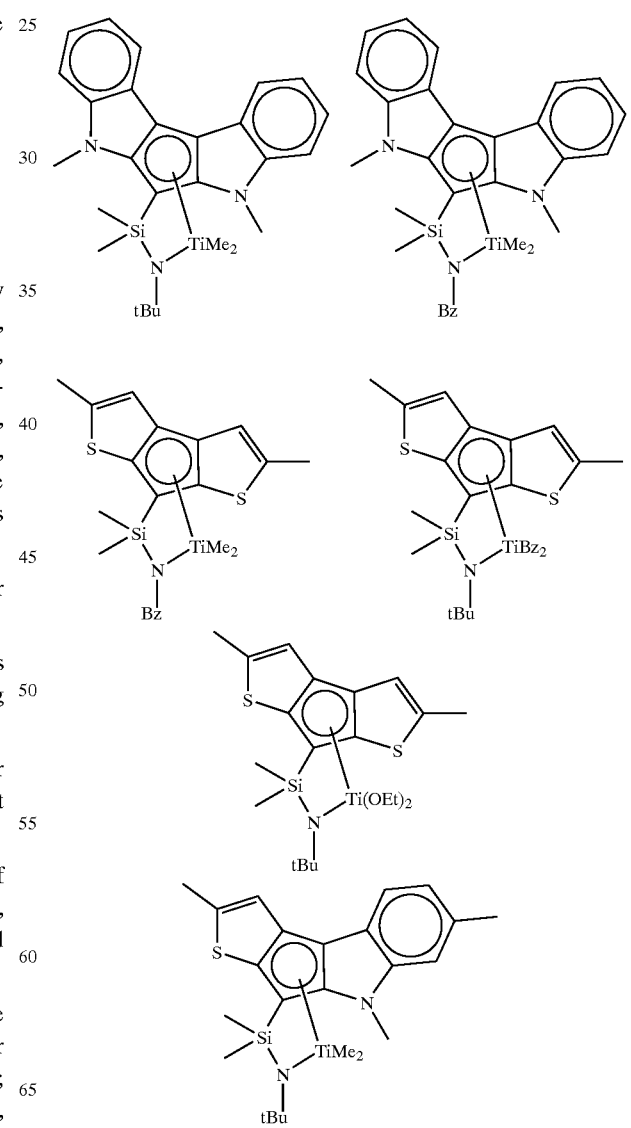

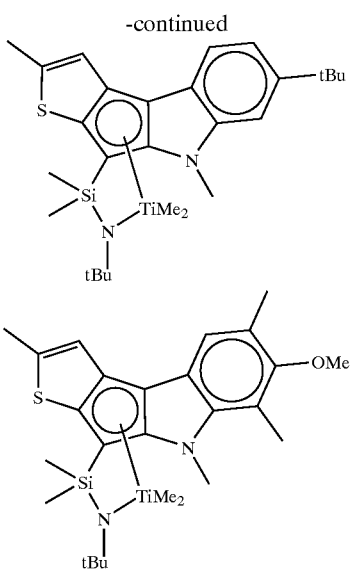

and the corresponding titanium dichloride or dimethoxy complexes.

The titanium complexes belonging to class (3) can be prepared starting from the ligand of formula (Va)

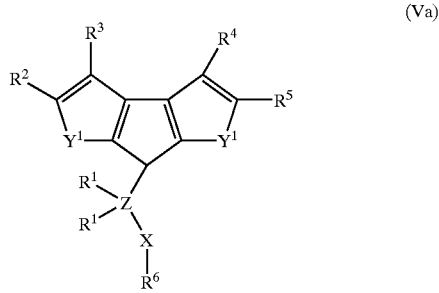

(Va)

wherein X, Z, $Y^1$, $R^1$, $R^2$, $R^3$, $R^4$, $R^5$ and $R^6$ have the meaning reported above.

The ligands of formula (II) can be prepared by a process comprising the following steps:

i) reacting a compound of formula (VI):

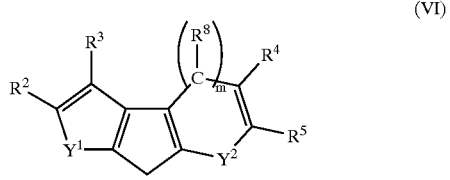

(VI)

wherein $Y^1$, m, $Y^2$, $R^2$, $R^3$, $R^4$, $R^5$, and $R^8$ have the meaning reported above,
with at least one equivalent of a base such as hydroxides and hydrides of alkali metals or alkaline-earth metals, metallic sodium and potassium or organolithium compounds such as butyllithium and methyllithium, and then contacting the obtained compound with a compound of formula $R^1{}_2ZY^3Y^4$, wherein $R^1$ and Z have the meaning reported above, $Y^3$ is a halogen atom preferably chlorine and $Y^4$ is an halogen atom preferably chlorine or a group $R^6XH$ wherein $R^6$ and X have the meaning reported above and H is hydrogen;

ii) if $Y^4$ is an halogen atom, reacting the obtained product with a compound of formula $R^6XH_2$ wherein $R^6$ and X have the meaning reported above and H is hydrogen and recovering the product.

Compound of formula VI can be prepared according to general procedures known in the state of the art, starting from commercially obtainable products or from derivatives which can be prepared by known methods. Synthesis of compounds of formula (VI) can be found for example in WO 99/24446, WO 01/48039, WO 01/48040 and WO 01/47939.

The ligand can be finally purified by general procedures known in the state of the art, such as crystallization or chromatography. All the steps are carried out in an aprotic solvent that can be a polar or apolar solvent. Not limitative examples of aprotic polar solvents which can be used in the above process are tetrahydrofurane, dimethoxyethane, diethylether and dichloromethane. Not limitative examples of apolar solvents suitable for the above process are toluene, pentane, hexane and benzene. The temperature in the various steps is preferably kept between −180° C. and 80° C., and more preferably between −20° C. and 40° C.

The titanium complexes of formula (I) can be prepared by first reacting a ligand of formula (II), prepared as described above, with a compound able to form a delocalized dianion, such as hydroxides and hydrides of alkali metals or alkaline-earth metals, metallic sodium and potassium or organo-lithium compounds such as butylithium, methylithium, on the cyclopentadienyl ring and on the group X, and thereafter with a compound of formula $TiL'_4$, wherein the substituents L' are halogen or —OR, wherein R has the meaning reported above. Non limiting examples of compounds of formula $TiL'_4$ are titanium tetrachloride and titanium tetramethoxy.

According to a preferred method, a ligand (II) is dissolved in an aprotic polar solvent and at least two equivalents of an organic lithium compound are added. The thus obtained anionic compound is added to a solution of the compound $TiL'_4$ in an aprotic solvent. At the end of the reaction, the solid product obtained is separated from the reaction mixture by techniques commonly used in the state of the art. Non limiting examples of aprotic polar solvents suitable for the above reported processes are tetrahydrofurane, dimethoxyethane, diethylether and dichloromethane. Not limiting examples of apolar solvents suitable for the above process are pentane, hexane and toluene. During the whole process, the temperature is preferably kept between −180° C. and 80° C., and more preferably between −20° C. and 40° C.

All the above processes are carried out in inert atmosphere such as nitrogen.

Titanium compounds of formula (I) in which at least one L substituent is different from halogen can be conveniently prepared by methods known in the state of the art for example, such compounds may be obtained by reacting the dihalogenated metallocene with alkylmagnesium halides (Grignard reagents) or with lithiumalkyl compounds.

When one or both L substituents are alkyl, the above titanium complexes (I) can be conveniently obtained by reacting directly a ligand of formula (II) with at least one molar equivalent of a compound of formula $TiCl_4$, in the presence of at least 3 molar equivalents of a suitable alkylating agent; said alkylating agent can be an alkaline or alkaline-earth metal, such as dialkyl-lithium, dialkyl-magnesium or a Grignard reagent, as described in WO 99/36427 and WO 00/75151.

An alternative process for preparing titanium complex of formula (I) in which both L substituents are OR groups comprises to prepare the titanium complex of formula (I) in which two L groups are R and then contact the obtained complex with oxygen. The resulting derivative having as L substituents two OR groups shows a better stability than the correspondent R substituted complex and therefore they can be stored for a long time without losing activity.

Suitable activating cocatalyst according to the process of the invention are alumoxanes or compounds able to form an alkyl metallocene cation.

Alumoxane useful as cocatalyst (B) may be linear alumoxanes of the formula (VII):

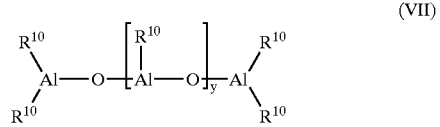
(VII)

wherein $R^{10}$ is selected from the group consisting of halogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl radicals and y ranges from 0 to 40; or cyclic alumoxanes of the formula (VIII):

(VIII)

wherein $R^{10}$ has the meaning described above and y is an integer ranging from 2 to 40.

The above alumoxanes may be obtained according to procedures known in the state of the art, by reacting water with an organo-aluminum compound of formula $AlR^{10}_3$ or $Al_2R^{10}_6$, with the condition that at least one $R^{10}$ is not halogen. In this case, the molar ratios of Al/water in the reaction is comprised between 1:1 and 100:1. Particularly suitable are the organometallic aluminum compounds of formula (II) described in EP 0 575 875 and those of formula (II) described in WO 96/02580. Moreover, suitable cocatalysts are those described in WO 99/21899 and in WO 01/21674.

The molar ratio between aluminum and the metal of the titanium complex is comprised between about 10:1 and about 5000:1, and preferably between about 100:1 and about 4000:1.

Examples of alumoxanes suitable as activating cocatalysts in the process of the invention are methylalumoxane (MAO), tetra-isobutyl-alumoxane (TIBAO), tetra-2,4,4-trimethylpentyl-alumoxane (TIOAO) and tetra-2-methyl-pentylalumoxane. Mixtures of different alumoxanes can also be used.

Not limiting examples of aluminum compounds of formula $AlR^{10}_3$ or $Al_2R^{10}_6$ are:
tris(methyl)aluminum, tris(isobutyl)aluminum,
tris(isooctyl)aluminum, bis(isobutyl)aluminum hydride,
methyl-bis(isobutyl)aluminum, dimethyl(isobutyl) aluminum,
tris(isohexyl)aluminum, tris(benzyl)aluminum,
tris(tolyl)aluminum, tris(2,4,4-trimethylpentyl)aluminum,
bis(2,4,4-trimethylpentyl)aluminum hydride, isobutyl-bis(2-phenyl-propyl)aluminum,
diisobutyl-(2-phenyl-propyl)aluminum, isobutyl-bis(2,4,4-trimethyl-pentyl)aluminum,
diisobutyl-(2,4,4-trimethyl-pentyl)aluminum, tris(2,3-dimethyl-hexyl)aluminum,
tris(2,3,3-trimethyl-butyl)aluminum, tris(2,3-dimethyl-butyl)aluminum,
tris(2,3-dimethyl-pentyl)aluminum, tris(2-methyl-3-ethyl-pentyl)aluminum,
tris(2-ethyl-3-methyl-butyl)aluminum, tris(2-ethyl-3-methyl-pentyl)aluminum,
tris(2-isopropyl-3-methyl-butyl)aluminum and tris(2,4-dimethyl-heptyl)aluminum.

Particularly preferred aluminum compounds are trimethylaluminum (TMA), tris(2,4,4-trimethylpentyl) aluminum (TIOA), triisobutylaluminum (TIBA), tris(2,3,3-trimethyl-butyl)aluminum and tris(2,3-dimethyl-butyl)aluminum.

Mixtures of different organometallic aluminum compounds and/or alumoxanes can also be used. In the catalyst system used in the process of the invention, both said titanium complex and said alumoxane can be pre-reacted with an organometallic aluminum compound of formula $AlR^{10}_3$ or $Al_2R^{10}_6$, wherein $R^{10}$ has the meaning reported above. Pre reaction time can vary from 20 seconds to 1 hour, preferably from 1 minute to 20 minutes.

Further activating cocatalysts suitable as component (B) in the catalysts of the invention are those compounds capable of forming an alkylmetallocene cation; preferably, said compounds have formula $Q^+W^-$, wherein $Q^+$ is a Brønsted acid capable of donating a proton and of reacting irreversibly with a substituent L of the compound of formula (I), and $W^-$ is a compatible non-coordinating anion, capable of stabilizing the active catalytic species which result from the reaction of the two compounds, and which is sufficiently labile to be displaceable by an olefinic substrate. Preferably, the $W^-$ anion comprises one or more boron atoms. More preferably, the anion $W^-$ is an anion of formula $BAr_4^{(-)}$, wherein the Ar substituents, equal to or different from each other, are aryl radicals such as phenyl, pentafluorophenyl, bis(trifluoromethyl)phenyl. Tetrakis-pentafluorophenyl-borate is particularly preferred. Moreover, compounds of formula $BAr_3$ can be conveniently used.

The catalysts system of the present invention can also be supported on an inert carrier (support), by depositing the titanium complex (A), or the reaction product of the titanium complex (A) with the cocatalyst (B), or the cocatalyst (B) and successively the titanium complex (A), on the inert support, such as silica, alumina, magnesium halides, olefin polymers or prepolymers (i.e. polyethylenes, polypropylenes or styrene-divinylbenzene copolymers). The thus obtained supported catalyst system, optionally in the presence of alkylaluminum compounds, either untreated or pre-reacted with water, can be usefully employed in gas-phase polymerization processes. The solid compound so obtained, in combination with further addition of the alkyl aluminum compound as such or prereacted with water, is usefully employed in gas phase polymerization.

The polymerization yield depends on the purity of metallocenes in the catalyst; the metallocene according to the present invention may be used as such or may be previously subjected to purification treatments.

Catalyst components (A) and (B) may be suitably contacted among them before the polymerization. The contact time may be comprised between 1 and 60 minutes, preferably between 5 and 20 minutes. The pre-contact concentrations for the titanium complex (A) are comprised between 0.1 and $10^{-8}$ mol/l, whereas for the cocatalyst (B) they are comprised between 2 and $10^{-8}$ mol/l. The precontact is generally carried out in the presence of a hydrocarbon solvent and, optionally, of small amounts of monomer.

The catalysts of the present invention are particularly advantageous in propylene polymerization, wherein they give substantially amorphous propylene polymers with high activities. When in the compounds of formula (I) $Y^1$ is $NR^7$ and preferably the compounds of formula (I) belong to classes (1) and (2), the propylene polymers obtained with the process of the invention have predominantly syndiotactic structure. The syndiotacticity of a polyolefins can be conveniently defined by the percent content of rr triads, as described in L. Resconi et al, Chemical Reviews, 2000, 100, 1253. When in the compounds of formula (I) $Y^1$ is $NR^7$ and preferably the compounds of formula (I) belong to classes (1) and (2), the propylene polymers obtained with the process of the present invention typically have triad contents in the range 60–80%, more preferably 65–75%. Their syndiotacticity is not high enough to produce substantial crystallinity (as measured by DSC), but it is high enough to generate resiliency in the polypropylene.

Being substantially void of crystallinity, their melting enthalpy ($\Delta H_f$) is preferably lower than about 20 J/g and even more preferably lower than about 10 J/g.

A further interesting use of the catalysts according to the present invention is directed to the preparation of propylene-based copolymers, wherein suitable comonomers are ethylene, alpha-olefins of formula $CH_2=CHR'$ wherein R' is a linear or branched, $C_2-C_{10}$ alkyl such as for example 1-butene, 1-pentene, 1-hexene, 4-methyl-1-pentene, non conjugate diolefins containing up to 20 carbon atoms, for examples said diolefins can belong to the formula $CH_2=CH-(CR''_2)_h-CR''_2=CR''$ wherein R" is hydrogen or a linear or branched, $C_1-C_{10}$ alkyl and h ranges from 1 to 15, such as 1,4-hexadiene, 1,5-hexadiene, 2-methyl-1,5-hexadiene, 7-methyl-1,6-octadiene, 1,7-octadiene, and the like or said olefins can be norbornene or its derivatives such as 5-ethylidene-2-norbornene.

The preferred ranges of composition depend on the type of polymer desired, and on the type of polymerization process employed. For example, in the case of amorphous copolymers of propylene with ethylene, such as those described in EP 729984, the content of ethylene ranges from 1 to 35% by moles preferably from 5 to 20% by moles. In the case of ethylene/propylene elastomers the content of propylene ranges from 20 to 80 wt %, preferably from 70 to 30 wt %, while in ethylene/propylene/diene elastomers the content of the diene, which preferably is ethylidenenorbornene or 1,4-hexadiene, range from 0.5 to 5 wt %.

Moreover, the molecular weight of the polymers can be varied by changing the polymerization temperature or the type or the concentration of the catalyst components, or by using molecular weight regulators, such as hydrogen, as well-known in the state of the art. The molecular weight of the propylene-based polymers may be also easily controlled by copolymerizing small amounts of ethylene.

The polymerization process according to the present invention can be carried out in gaseous phase or in liquid phase, optionally in the presence of an inert hydrocarbon solvent either aromatic (such as toluene), or aliphatic (such as propane, hexane, heptane, isobutane and cyclohexane).

The polymerization temperature ranges from about 0° C. to about 180° C., preferably from 40° C. to 120° C., more preferably from 60° C. to 90° C.

The molecular weight distribution can be varied by using mixtures of different metallocenes or by carrying out the polymerization in various steps differing in the polymerization temperature and/or in the concentration of the polymerization monomers.

The following examples are reported for illustrative and not limiting purposes.

GENERAL PROCEDURES AND CHARACTERIZATIONS

All operations were performed under nitrogen by using conventional Schlenk-line techniques. Solvents were purified by degassing with $N_2$ and passing over activated (8 hours, $N_2$ purge, 300° C.) $Al_2O_3$, and stored under nitrogen. The cocatalyst was a commercial MAO from Witco AG (10% wt solution in toluene).$Me_2Si(Me_4 Cp)(NtBu)TiCl_2$ was purchased from Witco AG.

$^1$H-NMR

The proton spectra of ligands and metallocenes were obtained using a Bruker DPX 200 spectrometer operating in the Fourier transform mode at room temperature at 200.13 MHz. The samples were dissolved in $CDCl_3$, $CD_2Cl_2$, $C_6D_6$ or $C_6D_5CD_3$. As a reference, the residual peak of $CHCl_3$, $CHDCl_2$, $C_6D_5H$ or $C_6D_5CH_3$ in the $^1$H spectra (7.25 ppm, 5.35 ppm, 7.15 and 2.10 ppm respectively) were used. Proton spectra were acquired with a 15° pulse and 2 seconds of delay between pulses; 32 transients were stored for each spectrum. All NMR solvents were dried over activated molecular sieves, and kept under nitrogen. Preparation of the samples was carried out under nitrogen using standard inert atmosphere techniques.

$^{13}$C-NMR

Carbon spectra were obtained using a Bruker DPX-400 spectrometer operating in the Fourier transform mode at 120° C. at 100.61 MHz. The samples were dissolved in $C_2D_2Cl_4$. The peak of the mmmm pentad in the $^{13}$C spectra (21.8 ppm) was used as a reference. The carbon spectra were acquired with a 90° pulse and 12 seconds of delay between pulses. About 3000 transients were stored for each spectrum. The ethylene content was determined according to M. Kakugo, Y. Naito, K. Mizunuma, T. Miyatake, Macromolecules 1982, 15, 1150. The 1-butene content was determined from the diad distribution, from the $S_{\alpha\alpha}$ carbons, as described in J. C. Randall, Macromolecules 1978, 11, 592.

GC-MS

GC-MS analyses were carried out on a HP 5890—series 2 gas chromatograph and a BP 5989B quadrupole mass spectrometer.

VISCOSITY MEASUREMENTS

The intrinsic viscosity (I.V.) was measured in tetrahydronaphtalene (T) at 135° C.

The polymer molecular weights were determined from the viscosity values.

DSC ANALYSIS

Melting point and heat of fusion measurements were carried out on a Perkin Elmer DSC 7 instrument by heating the sample from 25° C. to 200° C. at 10° C./min, holding for 2 min at 200° C., cooling from 200° C. to 25° C. at 10° C./min, holding for 2 min at 25° C., heating from 25° C. to 200° C. at 10° C./min. The reported values are those determined from the second heating scan. $T_g$ values were determined on a DSC30 Mettler instrument equipped with a cooling device, by heating the sample from 25° C. to 200° C. at 20° C./min, holding for 10 min at 200° C., cooling from 200° C. to −140° C., holding for 2 min at −140° C., heating from −140° C. to 200° C. at 20° C./min. The reported values are those determined from the second heating scan.

EXAMPLE 1 synthesis of Dimethylsilyl(tert-butylamido)(N-methyl-2-methyl-5,6-dihydroindeno[2,1-b]indol-6-yl)dimethyl titanium (B-1)

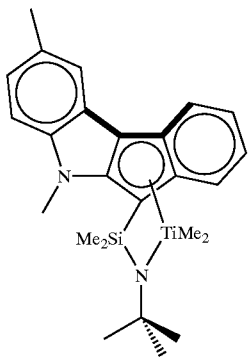

First Synthetic Route (a) Synthesis of 2-Methyl-5,6-dihydroindeno[2,1-b]indole

All operations were carried out in air, with out-of-the bottle solvents and reagents: isopropanol, RPE Carlo Erba (99%); 2-indanone, Chemische Fabrik Berg (98%); p-tolyl-hydrazine hydrochloride, Aldrich (98%).

In a 1-L jacketed glass reactor (Büchi) with magnetically driven, three blade stirrer, connected to a thermostat for temperature control, were charged 85.0 g of 2-indanone (Mw=132.16, 0.63 mol), 102.0 g of p-MeC$_6$H$_4$NHNH$_2$·HCl (Mw=158.63, 0.63 mol) and 0.5 L of i-PrOH. The thick suspension was warmed to 80° C. in about 30 minutes and the slurry darkened to dark brown under stirring. The mixture was stirred at 80° C. for 1 hour and then was cooled to room temperature in about 30 minutes.

The slurry was siphoned into 1.2 L of water containing 1.5 equivalents of NaHCO$_3$, thus obtaining a fine dispersion of a dark green product (no heat evolution was observed). The slurry was then filtered on a G3 frit, washed with water, dried in air under moderate vacuum, then in the rotating evaporator at 80° C. and finally under high vacuum (mechanical pump). 121.2 g of the target product were obtained with a yield of 87.3% (purity of 99.6% by G.C.)

$^1$H-NMR (CDCl$_3$, δ, ppm): 2.52 (s, 3H, CH$_3$); 3.70 (s, 2H, CH$_2$); 7.01–7.66 (m, 7H, Ar); 8.13 (bs, 1H, N-H).

(b) Synthesis of N-methyl-2-methyl-5,6-dihydroindeno[2,1-b]indole 10.2 g of 2-methyl-5,6-dihydroindeno[2,1-b]indole (Mw=219.28, purity 99.6%, 46.33 mmol), obtained as reported above, were dissolved in 100 mL of 1,3-dioxolane (Aldrich) at room temperature. 5.42 g of tert-BuOK (Fluka, 97%, Mw=112.22, 46.85 mmol) were then added; the solution changed color from green to dark brown and was stirred at room temperature for 10 minutes; then 2.90 mL of MeI (Mw=141.94, d=2.280, 46.58 mmol) were added. After 15 minutes of stirring, a solid started forming. Stirring was continued for 1 hour, then the reaction mixture was poured into water containing 4 g of NH$_4$Cl. The formed solid was isolated by filtration and dried in vacuo, to obtain 9.5 g of the target product as a microcrystalline brown solid in pure state, with a yield of 86.3% (purity of 98.2% by G.C.).

$^1$H-NMR (CDCl$_3$, δ, ppm): 2.52 (s, 3H, CH$_3$); 3.68 (s, 2H, CH$_2$); 3.78 (s, 3H, N—CH$_3$); 7.02–7.64 (m, 7H, Ar).

(c) Synthesis of Chlorodimethyl(N-methyl-2-methyl-5,6-dihydroindeno[2,1-b]indol-6-yl)silane 9.5 mL of a 2.5 M solution of n-BuLi in hexane (23.75 mmol) were added dropwise to a solution of 5.1 g of N-methyl-2-methyl-5,6-dihydroindeno[2,1-b]indole, obtained as reported above, (purity 98.2%, Mw=233.32, 21.46 mmol; indenoindole: n-BuLi=1:1.1) in 70 mL of THF, previously cooled to −78° C. At the end of the addition, the brown solution was allowed to warm up to room temperature and stirred for 6 hours. Then it was cooled again to −78° C. and added dropwise to a solution of dichlorodimethylsilane (Mw=129.06, d=1.064, 2.6 mL, 21.43 mmol; indenoindole: Me$_2$SiCl$_2$=1:1) in 20 mL of THF, previously cooled to −78° C. At the end of the addition, the reaction mixture was allowed to warm up to room temperature and stirred overnight. The solvents were evaporated under reduced pressure to give a brown sticky solid, which at the $^1$H-NMR analysis resulted to be the target product, with few by-products. The product was used in the subsequent step without further purification.

$^1$H-NMR (CDCl$_3$, δ, ppm): −0.13 (s, 3H, Si—CH$_3$); 0.48 (s, 3H, Si—CH$_3$); 2.53 (s, 3H, CH$_3$); 3.44 (s, 1H, CH); 3.88 (s, 3H, N—CH$_3$); 6.90–7.71 (m, 7H, Ar).

(d) Synthesis of 6-[Dimethylsilyl(tert-butylamino)]N-methyl-2-methyl-5,6-dihydroindeno[2,1-b]indole 3.96 g of chlorodimethyl(N-methyl-2-methyl-5,6-dihydroindeno[2,1-b]indol-6-yl)silane (Mw=325.92, 12.15 mmol), obtained as described above, were dissolved in 50 mL of toluene and added at −78° C. to a solution of t-BuNH$_2$ (3.0 mL, Mw=73.14, d=0.696, 28.55 mmol) in 20 mL of toluene. At the end of the addition, the reaction mixture was allowed to warm up to room temperature and stirred for 2 days to give a black suspension, which was filtered to remove the ammonium salt formed. The filtrate was concentrated under vacuum, obtaining 3.49 g of the target product, as a black sticky solid (raw yield=79.2%).

$^1$H-NMR (CDCl$_3$, δ, ppm): −0.15 (s, 3H, Si—CH$_3$); −0.04 (s, 3H, Si—CH$_3$); 1.23 (s, 9H, t-Bu); 2.52 (s, 3H, CH$_3$); 3.44 (s, 1H, CH); 3.86 (s, 3H, N—CH$_3$); 6.90–7.71 (m, 7H, Ar).

(e) Synthesis of Dimethylsilyl(tert-butylamido)(N-methyl-2-methyl-5,6-dihydroindeno[2,1-b]indol-6-yl) dimethyl Titanium 25.3 mL of a 1.6 M solution of MeLi in diethylether (40.48 mmol) were added dropwise at room temperature to a solution of 3.49 g of 6-[dimethylsilyl(tert-butylamino)]N-methyl-2-methyl-5,6-dihydroindeno[2,1-b]indole (Mw=362.60, 9.62 mmol), obtained as reported above, in 45 mL of Et$_2$O. The reaction mixture was stirred overnight: an increasing turbidity developed with final formation of a black suspension. Then 1.05 mL of TiCl$_4$ (Mw 189.71, d=1.730, 9.62 mmol) in 40 mL of pentane were slowly added at room temperature, and the resulting mixture was stirred overnight. The solvents were removed under reduced pressure to give a black sticky solid, which was extracted with 50 mL of toluene. The extract was then concentrated, yielding 3.02 g of the desired compound as a black powder (raw yield=71.6%).

$^1$H-NMR (C$_6$D$_6$, δ, ppm): −0.02 (s, 3H, Ti—CH$_3$); 0.07 (s, 3H, Ti—CH$_3$); 0.56 (s, 3H, Si—CH$_3$); 0.74 (s, 3H, Si—CH$_3$); 1.41 (s, 9H, t-Bu); 2.45 (s, 3H, CH$_3$); 3.12 (s, 3H, N—CH$_3$); 6.90–7.94 (m, 7H, Ar).

Second Synthetic Route (a) Synthesis of N-methyl-2-methyl-5,6-dihydroindeno[2,1-b]indole 22.37 g of 2-methyl-5,6-dihydroindeno[2,1-b]indole (99.6% by G.C., Mw=219.28, 101.6 mmol) were dissolved into 220 mL of 1,3-dioxolane (Aldrich) at room temperature and added of 11.46 g of t-BuOK (Aldrich, Mw=112.22, 101.6 mmol). The solution changed color from green to dark brown and was stirred at room temperature for 10 minutes; then 6.33 mL of MeI (Acros, Mw=141.94, d=2.280, 101.6 mmol) were added. After 15 minutes stirring, a solid started forming. Stirring was continued for 1 hour, then the reaction mire was poured into water containing 8 g of $NH_4Cl$ (Carlo Erba RPE, purity 99.5%). After two hours stirring, the formed solid was isolated by filtration and dried in vacuo to give 23.2 g of a brown powder, which was analyzed by NMR spectroscopy and GC-MS. The GC-MS analysis showed a purity in the desired product of 91.5% (yield= 89.5%). 2-methyl-5,6-dihydroindeno[2,1-b]indole and N-methyl-2,6-dimethyl-5,6-hydroindeno[2,1-b] indole were also present, in percentage of 2.6% and 3.7%, respectively.

An aliquot of the product (9.98 g) was suspended in 150 mL of MeOH (Carlo Erba RPE, purity 99.9%, b.p.=64.6° C.). After 30 min stirring at room temperature, a dark brown microcrystalline powder was isolated by filtration (9.18 g). The GC-MS analysis showed a higher purity (99.0%) in the desired product.

$^1$H NMR ($CDCl_3$, δ, ppm): 2.53 (s, 3H, $CH_3$); 3.65 (s, 2H, $CH_2$); 3.76 (s, 3H, N—$CH_3$); 7.00–7.60 (m, 7H, Ar).

$^{13}$C NMR ($CDCl_3$, δ, ppm): 21.52 ($CH_3$); 29.98 ($CH_2$); 31.08 (N—CH3); 109.38; 118.11; 119.13; 121.83; 122.14; 122.26; 124.62; 126.95; 129.11 (2C); 139.59; 140.50; 142.14; 148.87.

m/z (%): 233 (100) [M$^+$]; 218 (35).

(b) Synthesis of (tert-Butylamino)dimethylchlorosilane 15.7 mL of $Me_2SiCl_2$ (Mw=129.06, d=1.07, 130.21 mmol) in 20 mL of $Et_2O$ were added dropwise at 0° C. to a solution of 20.0 g of t-$BuNH_2$ (Mw=73.14, d=0.696, 273.44 mmol, t-$BuNH_2$: $Me_2SiCl_2$=2.1:1) in 40 mL of $Et_2O$. The resulting solution was allowed to warm up to room temperature and stirred for 1.5 hours. It was observed a colors change from yellow to light yellow with final formation of a white milky suspension. The latter was filtered and the filtrate concentrated in vacuo to give 18.93 g of a light yellow oil, which by $^1$H-NMR analysis appeared to be mainly the target product, together with a by-product, identified as di(t-butylamino)dimethylsilane. The silylamine was used in the subsequent step without further purification. Yield 65.8% (purity by $^1$H NMR=75.0% mol.)

$^1$H-NMR ($CD_2Cl_2$, δ, ppm): 0.48 (s, 6H, Si—$CH_3$); 1.26 (s, 9H, t-Bu); 1.42 (bs, 1H, NH).

(c) Synthesis of 6[Dimethylsilyl(tert-butylamino)]N-methyl-2-methyl-5,6-dihydro indeno[2,1-b]indole 6.66 mL of n-BuLi 2.5 M in hexane (16.65 mmol) were added dropwise at 0° C. to a solution of 3.53 g of N-methyl-2-methyl-5,6-dihydroindeno[2,1-b]indole (Mw=233.32, purity 99.0%, 15.13 mmol) in $Et_2O$. At the end of the addition, the reaction mixture was allowed to warm up to room temperature and stirred for two hours. Subsequently, 3.34 g of (tert-butylamino)dimethylchlorosilane (Mw= 165.74, purity 75.0% mol., d=0.887, 20.17 mmol) were added at 0° C. to the Li salt suspension and the resulting mixture was allowed to warm up to room temperature. After three hours stirring, the solvents were evaporated under reduced pressure and the residue was dissolved in 50 mL of toluene, obtaining a dark brown suspension, which was filtered. The filtrate was evaporated to dryness under reduced pressure, obtaining 5.86 g of a dark brown oil, which resulted to be 86.5% wt. pure (calculated by $^1$H-NMR). Yield=92.4%.

$^1$H-NMR ($C_6D_6$, δ, ppm): −0.14 (s, 3H, Si—$CH_3$); −0.13 (s, 3H, Si—$CH_3$); 0.99 (s, 9H, t-Bu); 2.54 (s, 3H, $CH_3$); 3.27 (s, 3H, N—$CH_3$); 3.40 (s, 3H, CH); 7.10–7.90 (m, 7R, Ar). m/z (%): 362 (39) [M$^+$]; 232 (16); 130 (100); 74 (18).

(d) Synthesis of Dimethylsilyl(tert-butylamido)(N-methyl-2-methyl-5,6-dihydroindeno[2,1-b]indol-6-yl)dimethyl Titanium 19.14 mL of a 1.6 M solution of MeLi in diethylether (30.63 mmol) were added dropwise at 0° C. to a solution of 2.76 g of 6-[dimethylsilyl(tert-butylamino)]N-methyl-2-methyl-5,6-dihydroindeno[2,1-b]indole (Mw=362.60, 7.62 mmol), obtained as reported above, in 40 mL of $Et_2O$. The resulting dark brown solution was allowed to warm up to room temperature and stirred for 1.5 hours. Then 0.84 mL of $TiCl_4$ (Mw=189.71, d=1.730, 7.63 mmol) in 4 mL of pentane were slowly added at room temperature and the resulting black suspension stirred for 1.5 hours. The solvents were removed under reduced pressure and the residue was extracted with 50 mL of toluene. The extract (3.07 g) was added of 70 mL of pentane, the resulting dark brown suspension stirred for 30 min at room temperature and filtered, giving as residue a light brown powder, which was dried and analyzed by $^1$H-NMR. The $^1$H-NMR analysis showed a purity of 97.0% wt. in the desired catalyst together with a 3.0% wt. of starting ligand. Yield=64.4% (2.22 g).

$^1$NMR ($C_6D_6$, δ, ppm): −0.02 (q, 3H, Ti—$CH_3$, J=0.36 Hz); 0.07 (q, 3H, Ti—$CH_3$, J=0.36 Hz); 0.55 (s, 3H, Si—$CH_3$); 0.74 (s, 3H, Si—$CH_3$); 1.39 (s, 9H, t-Bu); 2.43 (s, 3H, $CH_3$); 3.10 (s, 3H, N—$CH_3$); 6.91 (d, 1H, J=8.31 Hz); 7.02 (ddd, 1H, J=8.61, 6.87, 1.17 Hz); 7.13 (dq, 1H, J=8.31, 1.57, 0.59 Hz); 7.31 (ddd, 1H, J=8.26, 6.87, 0.96 Hz); 7.80 (dt, 1H, J=8.61, 0.96 Hz); 7.77–7.79 (m, 1H, Ar); 7.92 (dt, 1H, J=8.26, 1.17 Hz).

$^{13}$C-NMR ($C_6D_6$, δ, ppm): 6.91 (C-Si); 7.37 (C-Si); 21.66 ($CH_3$); 33.01 (N—$CH_3$); 34.62 (t-Bu); 55.56 (C-Ti); 57.24 (C-Ti); 68.74 (C-t-Bu); 109.43 (CH); 120.76 (CM); 124.17 (CH); 124.27 (CH); 125.22 (CH); 125.76 (CH); 128.44 (CH).

m/z (%) by "direct insertion probe" technique: 439 (32) [M$^+$+1]; 422 (100); 407 (26).

EXAMPLE 2

Synthesis of Dimethylsilyl(tert-butylamido)(N-methyl-2-methoxy-5,6-dihydroindeno[2,1-b]indol-6-yl)dimethyl Titanium (B-2)

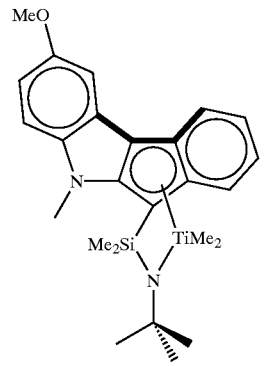

(a) Synthesis of 2-Methoxy-5,6-dihydroindeno[2,1-b] indole 8.21 g of 2-indanone (Aldrich, 98%, Mw=132.16, 60.88 mmol), 40 mL of isopropanol, 10.84 g of p-methoxyphenylhydrazin hydrochloride (Aldrich, 98%, Mw=174.63, 60.83 mmol) were charged at room temperature in a 250 mL flask equipped with magnetic stirrer. The slurry was brought to reflux (82° C.), (a black slurry was obtained), and kept at reflux for 1 hour. The dark brown viscous suspension was then cooled to room temperature; 200 mL of water saturated with NaHCO$_3$ were added into the reactor (final pH ca. 7.5–8), the resulting mixture was filtered and the residue washed with plenty of water. The dark green solid on the filter was dried in vacuo at 70° C. for 4 hours (14 g, 98.9% pure by GC, 96.7% yield of pure product).

$^1$H-NMR (CDCl$_3$, δ, ppm): 3.69 (s, 2H, CH$_2$); 3.93 (s, 3H, O—CH$_3$); 6.83–7.64 (m, 7H, Ar); 8.14 (bs, 1H, N-H).

(b) Synthesis of N-methyl-2-methoxy-5,6-dihydroindeno[2,1-b]indole 7.53 g of 2-methoxy-5,6-dihydroindeno[2,1-b]indole, obtained as reported above, (Mw=235.29, purity of 98.9%, 31.65 mmol) were dissolved in 60 mL of 1,3-dioxolane (Aldrich) at room temperature. 3.6 g of tert-BuOK (Fluka, Mw=112.22, 31.90 mmol) were added: the solution changed color from green to dark brown, and was stirred at room temperature for 10 min. Then 1.96 mL of MeI (Mw 141.94, d=2.280, 31.50 mmol) were added. After 10 min of stirring, a solid started forming. Stirring was continued for 1 hour, then the mixture was poured into water containing 5 g of NH$_4$Cl. The formed solid was isolated by filtration, the brown residue was dried in vacuo to obtain 7.85 g of microcrystalline brown solid: GC purity 85.8%, 85.2% yield of pure product.

$^1$H-NMR (CDCl$_3$, δ, ppm): 3.65 (s, 2H, CH$_2$); 3.75 (s, 3H, N—CH$_3$); 3.93 (s, 3H, O—CH$_3$); 6.85–7.61 (m, 7H, Ar).

(c) Synthesis of Chlorodimethyl(N-methyl-2-methoxy-5,6-dihydroindeno[2,1-b]indol-6-yl)silane 3.4 mL of a 2.5 M solution of n-BuLi in hexane (8.50 mmol) were added dropwise to a solution of 2.22 g of N-methyl-2-methoxy-5,6-dihydroindeno[2,1-b]indole, obtained as reported above, (Mw=249.32, purity 85.8%, 7.64 mmol; indenoindole: n-BuLi=1:1.1) in 50 mL of THF, previously cooled to −78° C. At the end of the addition, the brown solution was allowed to warm up to room temperature and stirred for 5 hours. Then it was cooled again to −78° C. and added dropwise to a solution of dichlorodimethylsilane (Mw=129.06, d=1.064, 0.92 mL, 7.64 mmol; indenoindole: Me$_2$SiCl$_2$=1:1) in 20 mL of THF, previously cooled to −78° C. At the end of the addition, the dark brown solution was allowed to warm up to room temperature and stirred overnight. The solvents were evaporated under reduced pressure to give the desired product, containing few by-products, in the form of a brown sticky solid; this product was used in the following step without further purification.

d) Synthesis of 6-[Dimethylsilyl(tert-butylamino)]N-methyl-2-methoxy-5,6-dihydro indeno[2,1-b]indole 3.25 g of crude chlorodimethyl(N-methyl-2-methoxy-5,6-dihydroindeno[2,1-b]indol-6-yl)silane (Mw=341.91, 9.50 mmol), obtained as reported above, were dissolved in 50 mL of toluene and added at −78° C. to a solution of t-BuNH$_2$ (2.3 mL, Mw=73.14, d=0.696, 21.89 mmol) in 20 mL of toluene. At the end of the addition, the reaction mixture was allowed to warm up to room temperature and stirred overnight to give a brown suspension, which was filtered to remove the ammonium salt formed. The filtrate was concentrated under vacuum to give 2.18 g of the desired product as a brown sticky solid (raw yield=60.6%). This product was used in the next step without further purification.

$^1$H-NMR (CDCl$_3$, δ, ppm): −0.14 (s, 3H, Si—CH$_3$); −0.02 (s, 3H, Si—CH$_3$); 1.23 (s, 9H, t-Bu); 3.86 (s, 3H, N—CH$_3$); 3.926 (s, 1H, CH); 3.934 (s, 3H, O—CH$_3$); 6.80–7.70 (m, 7H, Ar).

The fraction insoluble in toluene was extracted with 30 mL of CH$_2$Cl$_2$ and 0.58 g of the by-product bis(N-methyl-2-methoxy-5,6-dihydroindeno[2,1-b]indol-6-yl)dimethyl silane, formed in the previous step, were isolated as a light brown powder (13.7% yield towards starting N-methyl-2-methoxy-5,6-dihydroindeno[2,1-b]indole).

$^1$H-NMR (CDCl$_3$, δ, ppm): −0.23 (s, 6H, Si—CH$_3$); 3.35 (s, 6H, N—CH$_3$); 3.91 (s, 6H, O—CH$_3$); 3.93 (s, 2H, CH); 6.82–7.63 (m, 14H, Ar).

(e) Synthesis of Dimethylsilyl(tert-butylamido)(N-methyl-2-methoxy-5,6-dihydroindeno[2,1-b]indol-6-yl) Dimethyl Titanium 15.6 mL of a 1.6 M solution of MeLi in diethylether (24.96 mmol) were added dropwise at room temperature to a solution of 2.18 g of 6-[dimethylsilyl(tert-butylamino)]N-methyl-2-methoxy-5,6-dihydroindeno[2,1-b]indole (Mw=378.58, 5.76 mmol), obtained as reported above, in 45 mL of Et$_2$O. The reaction mixture was stirred for 5 hours at room temperature with final formation of a dark brown suspension. Then 0.65 mL of TiCl$_4$ (Mw=189.71, d=1.730, 5.93 mmol) in 20 mL of pentane were slowly added at room temperature, and the resulting mixture was stirred overnight. The solvents were removed under reduced pressure to give a black solid, which was extracted with 35 mL of toluene. The extract was concentrated yielding 1.16 g of the target product as a brown powder (raw yield=44.3%).

$^1$H-NMR (C$_6$D$_6$, δ, ppm): −0.01 (s, 3H, Ti—CH$_3$); 0.04 (s, 3H, Ti—CH$_3$); 0.55 (s, 3H, Si—CH$_3$); 0.74 (s, 3H, Si—CH$_3$); 1.40 (s, 9H, t-Bu); 3.09 (s, 3H, N—CH$_3$); 3.55 (s, 3H, O—CH$_3$); 6.82–7.92 (m, 711, Ar).

EXAMPLE 3

Synthesis of Dimethylsilyl(tert-butylamido)(N-methyl-2-methyl-1,8-dihydroindeno[2,1-b]pyrrol-6-yl)dimethyl Titanium (B-3)

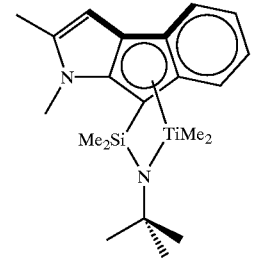

(a) N-methyl-2-methyl-1,8-dihydroindeno[2,1-b]pyrrole was prepared according to the protocol described in Patent Application WO 99/24446.

(b) Synthesis of 8-[Dimethylsilyl(tert-butylamino)]N-methyl-2-methyl-1,8-dihydroindeno[2,1-b]pyrrole 18 mL of 1.6 M solution of BuLi (28.8 mmol) in hexane was added dropwise to a solution of 3.5 g of N-Me-2-Me-indenopyrrole (19 mmol) in 60 mL of ether at −30° C. At the end of the addition the solution was allowed to warm up to room temperature and stirred for 4 hours. Then it was cooled again to −30° C. and treated with 5 mL of Me$_2$SiCl$_2$ (42 mmol) in 5 mL of ether. The mixture was allowed to warm up to room temperature and stirred overnight. The resulting suspension was filtered, the solvent was evaporated in vacuum. The crude product was dissolved in 50 mL of ether and then was treated dropwise with 17.5 mL (167 mmol) of t-butylamine at −20° C. The resulting mixture was allowed to warm up to room temperature and then stirred overnight.

The solution was isolated by filtration and the solvent was evaporated to give the silyl-amine as a reddish-brown oil. Yield 4.67 g (83%).

$^1$H NMR (toluene-d$^8$): 7.48 (d, 1H); 7.44 (d, 1H); 7.23 (t, 1H); 7.05(t, 1H); 6.18 (1H); 3.12 (s, 3H); 2.15 (s, 3H); 1.02 (s, 9H); −0.11 (s, 3H); −0.12 (s, 3H).

(c) Synthesis of Dimethylsilyl(tert-butylamido)(N-methyl-2-methyl-1,8-dihydroindeno[2,1-b]pyrrol-6-yl) Dimethyl Titanium 49 mL of a 1.33 M solution of MeLi in diethyl ether (65.2 mmol) were added dropwise at −20° C. to a solution of 4.15 g of 8-[dimethylsilyl(tert-butylamino)]-N-methyl-2-methyl-indenopyrrole (14 mmol) in 60 mL of ether. The reaction mixture was stirred overnight and then was cooled to −30° C. and was treated with 1.54 mL of TiCl$_4$ (14 mmol) in 60 mL of hexane. The resulting black mixture was stirred overnight, then it was evaporated and added with 60 mL of toluene. Then the reaction mixture was evaporated and the residue was extracted twice with 50 mL of toluene. The resulting solution was evaporated to a volume of 15 mL and kept at room temperature for 15 hours. Red crystals were isolated, washed twice with 10 mL of cooled pentane and dried. Yield 2.1 g.

$^1$H NMR (toluene-d$^8$): 7.68 (d, 1H); 7.61 (d, 1H); 7.20 (dd, 1H); 6.94 (dd, 1H); 6.13 (s, 1H); 2.88 (s, 3H); 1.98 (s, 3H); 1.41 (s, 9H); 0.73 (s, 3H); 0.51 (s, 3H); 0.05 (s, 3H); −0.04 (s, 3H)

EXAMPLE 4

Synthesis of Dimethylsilyl(tert-butylamido)(N-ethyl-5,6-dihydroindeno[2,1-b]indol-6-yl)dimethyl Titanium (B-4)

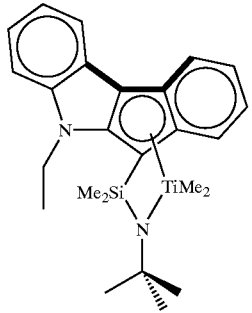

(a) Synthesis of 5,6-Dihydroindeno[2,1-b]indole

In a 1-L flask were charged 36.55 g of 2-indanone (Aldrich, Mw=−132.16, 276.6 mmol), 40.00 g of phenylhydrazine hydrochloride (Aldrich, 99%, Mw=144.61, 276.6 mmol) and 0.3 L of i-PrOH. The suspension was warmed to 80° C. in about 30 minutes and the slurry changed color from yellow to dark brown under stirring. The reaction mixture was stirred at 80° C. for 1.5 hours and then was cooled to room temperature in about 30 minutes. The slurry was siphoned into 1.0 L of water containing 34.85 g of NaHCO$_3$, thus obtaining a fine dispersion of a green product (no heat evolution was observed). The slurry was then filtered on a G4 frit, washed with water, dried in air under moderate vacuum for 24 h until to achieve constant weight.

52.81 g of the target product as a green powder were obtained with a yield of 92.8% (purity of 99.8% by G.C.)

$^1$H-NMR (CDCl$_3$, δ, ppm): 3.72 (s, 2H, CH$_2$); 7.12 (td, 1H, H8, J=7.48, 1.17 Hz); 7.16–7.29 (m, 2H, H2, H3); 7.31–7.39 (m, 2H, H1, H9); 7.42 (dt, 1H, H7, J=7.24 Hz); 7.66 (dt, 1H, H10, J=7.48 Hz); 7.85–7.89 (m, 1H, H4); 8.26 (bs, 1H, N-H).

$^{13}$C-NMR (CDCl$_3$, δ, ppm): 31.51 (CH$_2$); 112.18 (C-H1); 118.77 (C-H10); 119.56 (C-H4); 120.73, 121.84 (C-H2, C-H3); 122.47 (C10c); 122.91 (C-H8); 125.05 (C-H7); 127.38 (C-H9); 140.32 (C10b); 140.93 (C4a); 142.88 (C6a, 10a); 146.44 (C5a).

(b) Synthesis of N-Ethyl-5,6-dihydroindeno[2,1-b]indole 15.00 g of 5,6-dihydroindeno[2,1-b]indole (99.8% by G.C., Mw=205.26, 73.1 mmol) were dissolved into 200 mL of 1,3-dioxolane (Aldrich) at room temperature in a 0.5-L flask. 8.28 g of t-BuOK (Fluka, 99%, Mw=112.22, 73.1 mmol) were added and the reaction mixture turned from a green suspension to a brown solution. After 30 min stirring at room temperature, 5.51 mL of EtBr (Fluka, 99%, Mw=108.97, d=1.46, 73.1 mmol) were added, obtaining a brown suspension. Stirring was continued for 2 hours, then the reaction mixture was poured into water containing 8 g of NH$_4$Cl (Carlo Erba RPE, purity 99.5%). After two hours stirring, the green-brown suspension was filtered on a G4 frit, the solid dried in air under moderate vacuum to give a green powder (8.98 g), which was analyzed by $^1$H NMR. Purity 98.9% wt. by $^1$H NMR (yield=52.1%).

$^1$H-NMR (CDCl$_3$, δ, ppm): 1.48 (t, 3H, CH$_3$, J=7.26 Hz); 3.73 (s, 2H, CH$_2$); 4.24 (q, 2H, CH$_2$, J=7.26 Hz); 7.04–7.90 (m, 8H, Ar).

(c) Synthesis of (tert-Butylamino)dimethylchlorosilane 15.95 mL of Me$_2$SiCl$_2$ (Mw=129.06, 99%, d=1.064, 130.21 mmol) in 20 mL of Et$_2$O were added dropwise at 0° C. to a solution of 20.41 g of t-BuNH$_2$ (Mw=73.14, 98%, d=0.696, 273.45 mmol, t-BuNH$_2$: Me$_2$SiCl$_2$=2.1:1) in 40 mL of Et$_2$O. The resulting milky suspension was allowed to warm up to room temperature and stirred for 30 min. The solvent was removed and the residue extracted with 50 mL of pentane, to give 13.76 g of a colorless oil, which by $^1$H-NMR analysis appeared to be the target product 83.7% wt. pure, together with 16.3% wt. of di(t-butylamino) dimethylsilane. The silylamine was used in the subsequent step without further purification. Yield 53.4%.

$^1$H-NMR (CDCl$_3$, δ, ppm): 0.44 (s, 6H, Si—CH$_3$); 1.21 (s, 9H, t-Bu).

(d) Synthesis of 6-[Dimethylsilyl(tert-butylamino)]ethyl-5,6-dihydro indeno[2,1-b]indole 8.02 mL of n-BuLi 2.5 M in hexane (20.04 mmol) were added dropwise at 0° C. to a solution of 4.30 g of N-ethyl-5,6-dihydroindeno[2,1-b]indole (Mw=233.31, purity 98.9%, 18.22 mmol) in Et$_2$O. At the end of the addition, the reaction mixture was allowed to warm up to room temperature and stirred for two hours. The dark brown solution obtained was added at 0° C. to a solution of 4.32 g of (tert-butylamino) dimethylchlorosilane (Mw=165.74, purity 83.7% wt., d=0.887, 21.86 mmol) in Et$_2$O. The final mixture was allowed to warm up to room temperature and stirred for three hours. Then the solvents were evaporated under reduced pressure to give a residue (8.73 g) which was extracted with 50 mL of toluene. The extract, a sticky brown solid (7.48 g), was washed with pentane obtaining 4.32 g of a light brown powder, which was analyzed by $^1$H-NMR. The $^1$H-NMR analysis showed a purity of 96.6% wt. in the desired ligand together with a 3.4% wt. of starting N-ethyl-5,6-dihydroindeno[2,1-b]indole. Yield=63.1%.

$^1$H-NMR (C$_6$D$_6$, δ, ppm): −0.23 (s, 3H, Si—CH$_3$); −0.01 (s, 3H, Si—CH$_3$); 0.41 (bs, 1H, NH); 0.99 (s+t, 12H, t-Bu+CH$_3$); 3.56 (s, 1H, CH); 4.07 (m, 2H, CH$_2$); 7.15–8.07 (m, 8H, Ar).

$^1$H-NMR (CDCl$_3$, δ, ppm): −0.13 (s, 3H, Si—CH$_3$); 0.03 (s, 3H, Si—CH$_3$); 0.75 (bs, 1H, NH); 1.26 (s, 9H, t-Bu); 1.37

(t, 3H, CH$_3$, J=7.14 Hz); 3.84 (s, 1H, CH); 4.50 (m, 2H, CH$_2$); 6.90–8.00 (m, 8H, Ar).

(e) Synthesis of Dimethylsilyl(tert-butylamido)(N-ethyl-5,6-dihydroindeno[2,1-b]indol-6-yl)dimethyl Titanium 16.13 mL of a 1.6 M solution of MeLi in diethylether (25.80 mmol) were added dropwise at 0° C. to a solution of 2.30 g of 6-[dimethylsilyl(tert-butylamino)]N-ethyl-5,6-dihydroindeno[2,1-b]indole (Mw=362.60, 6.34 mmol), obtained as reported above, in 40 mL of Et$_2$O. The resulting dark brown suspension was allowed to warm up to room temperature and stirred for 3 hours. Then 0.70 mL of TiCl$_4$ (Mw=189.71, d=1.730, 6.34 mmol) in 4 mL of pentane were slowly added at room temperature and the resulting dark brown suspension stirred for 1 hour. The solvents were removed under reduced pressure and the residue (4.63 g) was extracted with 50 mL of toluene. The extract (2.27 g of a sticky dark brown powder) was washed with pentane and the residue dried giving a brown powder (1.7 g), which was analyzed by $^1$H-NMR. The $^1$H-NMR analysis showed a purity of 97.6% wt. in the desired catalyst together with a 2.4% wt. of starting ligand. Yield=79.7%.

$^1$H-NMR (C$_6$D$_6$, δ, ppm): −0.002 (q, 3H, Ti—CH$_3$, J=0.41 Hz); 0.09 (q, 3H, Ti—CH$_3$, J=0.41 Hz); 0.61 (s, 3H, Si—CH$_3$); 0.73 (s, 3H, Si—CH$_3$); 1.05 (t, 3H, CH$_3$, J=7.26); 1.41 (s, 9H, t-Bu); 3.78 (q, 2H, CH$_2$, J=7.26 Hz); 6.98–7.06 (m, 2H, H3, H8); 7.24–7.33 (m, 3H, H1, H4 and H9); 7.80 (dt, 1H, J=8.67 Hz, H7); 7.88–7.93 (m, 2H, H2, H10).

$^{13}$C-NMR (C$_6$D$_6$, δ, ppm): 6.62 (Si—CH$_3$); 7.63 (Si—CH$_3$); 14.48 (CH$_3$); 34.51 (t-Bu); 40.00 (CH$_2$); 56.90 (Ti—CH$_3$); 57.01 (Ti—CH$_3$); 57.81 (C-t-Bu); 67.98 (C-Si); 109.81 (C-H3); 114.56 (C-H10c); 120.48 (C-H1); 120.59 (C-H2); 123.67 (C-10a); 124.08 (C-H10); 124.32 (C-H8); 124.49 (C-H4); 125.27 (C-H9); 128.62 (C-H7); 134.89 (C6a); 145.50 (C4a); 147.34 (C5a).

EXAMPLE 5

Synthesis of Dimethylsilyl(tert-butylamido)(2,5-dimethyl-7H-thieno[3',2':3,4]cyclopenta[1,2-b]thiophen-7-yl)dimethyl Titanium (A-1).

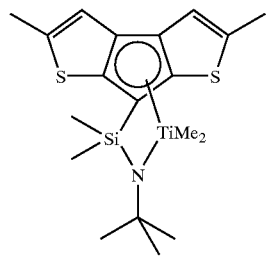

a) Chloro(2,5-dimethyl-7H-thieno[3',2':3,4]cyclopenta[1,2-b]thiophen-7-yl)dimethylsilane.

A suspension of 4.13 g (20 mmol) 2,5-dimethyl-7H-cyclopenta[1,2-b:4,3-b']-dithiophene in 80 ml ether was treated dropwise with 15 ml (24 mmol, 20% excess) 1.6M BuLi in hexane at −40° C. under stirring. The mixture was stirred for 3 h, and then treated with 4.82 ml (40 mmol) Me$_2$SiCl$_2$ in 10 ml Et$_2$O. The precipitate was filtered and used without further purification. Yield 4.84 g (81%), taking into consideration the presence of LiCl (1.02 g, 24 mmol).

$^1$H NMR (CDCl$_3$, 30° C.) δ: 6.85 (q, 2H), 3.93 (s, 1H), 2.57 (bs, 6H), 0.25 (s, 6H).

b) N-(tert-Butyl)(2,5-dimethyl-7H-thieno[3',2':3,4]cyclopenta[1,2-b]thiophen-7-yl) Dimethylsilanamine.

A solution of 2.12 ml (20 mmol) tert-butylamine in 70 ml ether was treated dropwise with 12.5 ml (20 mmol) 1.6M BuLi in hexane at −30° C. The reaction mixture was stirred at r.t. for 3 h and the resulting suspension was treated with a solution of 4.84 g (16.2 mmol) chloro(2,5-dimethyl-7H-thieno[3',2':3,4]cyclopenta[1,2-b]thiophen-7-yl) dimethylsilane in 30 ml ether at −70° C. The resulting suspension was allowed to warm to r.t. and was stirred overnight. The solution was separated from LiCl and evaporated. Yield 4.47 g (82%) of brown solid that was used without further purification.

$^1$H NMR (CDCl$_3$, 30° C.) δ: 6.85 (q, 2H), 3.80 (s, 1H), 2.58 (bs, 6H), 1.31 (s,9H), 0.05 (s, 6H).

c) Me$_2$Si(t-BuN)(2,5-dimethyl-7H-thieno[3',2':3,4]cyclopenta[1,2-b]thiophen-7-yl) TiMe$_2$.

To a solution of 1.93 g (5.7 mmol) N-(tert-butyl)(2,5-dimethyl-7H-thieno[3',2':3,4]cyclopenta[1,2-b]thiophen-7-yl)dimethylsilanamine in 30 ml ether 23 ml (28.7 mmol) 1.2M MeLi in ether was added at −40° C. under stirring. Then the reaction mixture was stirred under reflux for 3 h. The resulting mixture was cooled to −60° C. and the solution of 0.63 ml (5.7 mmol) TiCl$_4$ in 30 ml hexane was added. The mixture was allowed to warm and was stirred overnight The resulting mixture was evaporated, the residue was extracted with hexane (3 times with 50 ml). The hexane solution was concentrated to a volume of 10 ml and kept for 10 hours at r.t. The crystalline product was separated from the mother solution, washed twice with cold pentane and dried. Yield 0.27 g (11%) of dark red crystals.

$^1$H NMR (C$_7$D$_8$, 30° C.) δ: 6.76 (q, 2H), 2.20 (d, 6H), 1.49 (s, 9H), 0.56 (s, 6H), 0.36 (s, 6H).

$^{13}$C NMR (C$_7$D$_8$, 30° C.) δ: 146.51, 139.67, 133.08, 116.65, 78.16, 58.00, 56.82, 34.56, 16.29 3.21.

EXAMPLE 6

Synthesis of Dimethylsilyl(tert-butylamido)(indenyl)dimethyl Titanium (C-3)

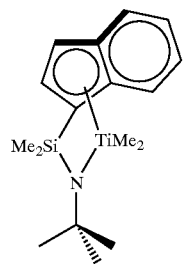

11.3 mL of a 1.6 M solution of methyllithium in diethyl ether (18.04 mmoles) were slowly added at −78° C. to a solution of 1.08 gram (4.40 mmoles) of IndMe$_2$SiNH$^t$Bu in 23 mL of diethyl ether. During the addition an increasing turbidity develops with final formation of a yellow suspension. This mixture was allowed to warm to room temperature and stirred for two hours.

0.5 mL of TiCl$_4$ (4,40 mmoles) were diluted in 23 mL of pentane. This solution was added very slowly and cautiously to the Li salt suspension in diethyl ether at room temperature. The resulting dark suspension was stirred at room temperature overnight. The reaction mixture was then brought to dryness under reduced pressure. The dark solid was extracted with 60 mL of toluene and then the filtrate was evaporated to dryness under reduced pressure to give 0.99 g (70% yield) of a gray-black solid. $^1$H NMR confirms formation of [Me$_2$Si(Ind)(t-BuN)]TiMe$_2$.

$^1$H NMR (C$_6$D$_6$, δ, ppm): −0.15 (q, J=0.48 Hz, 3H, Ti—CH$_3$), 0.36 (s, 3H, Si—CH$_3$), 0.53 (s, 3H, Si—CH$_3$), 0.82 (q, J=0.48 Hz, 3H, Ti—CH$_3$), 1.44 (s, 9H, t-Bu); 6.05 (d, J=3.21 Hz, 1H, Cp-H2); 6.88 (ddd, J=8.50, 6.64, 1.04 Hz, 1H, Ar-H6); 7.01 (dd, J=3.21, 0.83 Hz, 1H, Cp-H3); 7.07 (ddd, J=8.50, 6.64, 1.04 Hz, 1H, Ar-H5); 7.46 (dq, J=8.50, 1.04 Hz, 1H, Ar-H7); 7.48 (dt, J=8.50, 1.04 Hz, 1H, Ar-H4).

EXAMPLE 7

Synthesis of Dimethylsilyl(tert-butylamido)(2-methyl-indenyl)dimethyl Titanium (C-4)

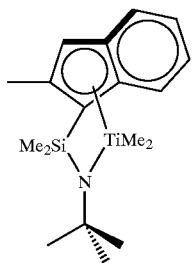

The complex dimethylsilyl(tert-butylamido)(2-methyl-1-indenyl) dimethyl titanium was prepared from the corresponding ligand in 71%, by using the same procedure.

(a) Synthesis of (2-Me-Ind)SiMe$_2$($^t$BuNH)

5.02 g of (2-Me Ind)SiMe$_2$Cl (25.53 mmol) in Et$_2$O were added at 0° C. to a solution of $^t$BuNH$_2$ (56.16 mmol) to give a yellow slurry. The mixture was stirred at room temperature for 16 h. The solvents were evaporated under reduced pressure, and the product extracted with toluene to give, after filtration and evaporation of the solvent, 5.52 g of an orange oil. $^1$H NMR analysis shows the presence of the two isomers (allylic, 60%, vinylic, 40%). Yield 83.4%.

$^1$H-NMR (C$_6$D$_6$, δ, ppm), allylic isomer: −0.09 (s, 3H, Si—CH$_3$); 0.11 (s, 3H, Si—CH$_3$); 1.02 (s, 9H, $^t$Bu); 2.14 (s, 3H, CH$_3$); 3.21 (s, 1H, C-H); 6.52 (s, 1H, C-H); vinylic isomer: 0.46 (s, 6H, Si—CH$_3$); 1.1 (s, 9H, $^t$Bu); 2.06 (s, 3H, CH$_3$); 3.05 (s, 2H, CH$_2$); both isomers: 6.98–7.82 (m, 8H, Ar);

(b) Synthesis of Me$_2$Si(2-Me-Ind)($^t$BuN)TiMe$_2$ 25 mL of MeLi 1.6 M in Et$_2$O (40 mmol) were added at 0° C to a solution of 2.53 g of (2-Me Ind)SiMe$_2$($^t$BuNH) (9.75 mmol), after 1.5 h stirring at room temperature were added 1.07 mL of TiCl$_4$ in pentane (9.75 mmol). After 2 h the solvents were removed under reduced pressure, the mixture taken up in 50 mL of toluene, stirred 30 min, and filtered to give, after evaporation of the solvent, 2.68 g of dark brown powder. The powder was taken up in pentane, filtered, and the filtrated brought to dryness under reduced pressure to give 2.31 g of ochra powder. Yield 70.6%.

$^1$H-NMR (C$_6$D$_6$, δ, ppm): −0.11 (q, 3H, J=0.48 Hz, Ti—CH$_3$); 0.46 (bs, 3H, Si—CH$_3$); 0.56 (bs, 3H, Si—CH$_3$); 0.85 (q, 3H, J=0.48 Hz, Ti—CH$_3$); 1.47 (s, 9H, $^t$Bu); 1.99 (s, 3H, CH$_3$); 6.76 (bs, 1H, H3); 6.89 (ddd, 1H, H6, J=8.41, 6.77, 1.08 Hz); 7.07 (ddd, 1H, H5, J=8.41, 6.77, 1.08 Hz); 7.44 (dt, 1H, H4, J=8.41, 1.08 Hz); 7.51 (dq, 1H, H7, J=8.41, 1.08 Hz).

$^{13}$C-NMR (C$_6$D$_6$, δ, ppm): 5.30 (C-Si); 5.55 (C-Si); 17.98 (CH$_3$); 33.85 ((CH$_3$)$_3$); 50.82 (C-Ti); 56.57 (C-Ti); 57.55 (C-$^t$Bu); 115.64 (C-H3); 124.72 (C-H6); 124.9 (C-H4); 125.17 (C-H5); 127.81 (C-H7); 131.57 (C-C3a); 133.82 (C-C7a); 140.97 (C—CH$_3$).

EXAMPLE 8

Preparation of the Supported Catalyst

Polyethylene (PE) used as carrier has particles diameter of 250–300 μm, porosity measured with Mercury porosimeter technique (MA 17302) is about 50% V/V, the surface area is 5.6 m$^2$/g and the average diameter of pores is 8923 Å.

Impregnation

The apparatus used for the supportation is a glass cylindrical vessel, equipped with a vacuum pump, a dosing pump for the feeding of the catalytic solution on the carrier and a stirrer to allow a good mixing during the impregnation step. The preparation of the supported catalysts is carried out under nitrogen flow at room temperature.

5 g of the PE carrier described above is loaded into the vessel and mechanically stirred under nitrogen flow, 3 ml of a MAO solution (Witco, 100 g/l in toluene) is dosed in a single addition step on the prepolymer to scavenge residual impurities, in order to reach the incipient wetness. The solvent is then evaporated under vacuum.

The catalytic solution is prepared by dissolving 17 mg of B-4 in 9 ml of the same MAO solution, with the aim of achieving an Al/Ti=400 mol/mol. After stirring for 15 minutes, this solution is added to the carrier in 3 aliquots; after each addition, once reached the incipient wetness, the solvent is evaporated under vacuum.

The analysis of the obtained supported catalysts are Al=7.3%, Ti=0.03%.

Polymerization Tests

Batch polymerizations were carried out in a 1-L or 4.25-L stainless-steel stirred reactor. The reactor was purified by washing with a hexane solution of TIBA (Al(i-Bu)$_3$), and then dried by purging with propylene at 80° C. for one hour. The catalyst/cocatalyst mixture was prepared by dissolving the Ti complex in the required amount of MAO/toluene solution, and aged 10 min.

EXAMPLES 9–11

Propylene polymerization

MAO (commercial product by Witco, 10% w/w in toluene, 1.7 M in Al) was used as received. The catalyst system was prepared by dissolving the amount of dimethylsilyl(tert-butylamido)(N-methyl-2-methyl-5,6-dihydroindeno[2,1-b]indol-6-yl)dimethyl titanium (B-1) prepared according example 1, first synthetic route, as reported in Table 1, with the amount of MAO reported in Table 1; the obtained solution was stirred for 10 minutes at room temperature, before being injected into the autoclave.

1 mmol of Al(i-Bu)$_3$ (TIBA) (as a 1 M solution in hexane) and 300 g of propylene were charged, at room temperature, in a 1-L jacketed stainless-steel autoclave, equipped with magnetically driven stirrer and a 35-mL stainless-steel vial, connected to a thermostat for temperature control, previously purified by washing with an Al(i-Bu)$_3$ solution in hexane and dried at 50° C. in a stream of propylene. The autoclave was then thermostatted at 2° C. below the polymerization temperature and the catalyst system, prepared as reported above, was injected in the autoclave by means of nitrogen pressure through the stainless-steel vial. The temperature was rapidly raised to the polymerization temperature, as indicated in Table 1, and the polymerization was carried out at constant temperature, for the time reported in Table 1.

After venting the unreacted monomer and cooling the reactor to room temperature, the polymer was dried under reduced pressure, at 60° C.

The polymerization data and the characterization data of the obtained polymers are reported in Table 1.

The obtained results demonstrate that the titanium complexes according to the present invention may give high molecular weight amorphous polypropylene.

EXAMPLE 12

Propylene Polymerization

Propylene polymerization was carried out according to the procedure reported in Examples 9–11, with the difference that B-1 obtained according example 1, second synthetic route, was used as catalyst.

Polymerization data, yields and characteristics of the obtained polymer are reported in Table 1.

EXAMPLE 13

Influence of Hydrogen

In order to evaluate the influence of hydrogen on the molecular weight of the obtained polymers, propylene polymerization was carried out according to the procedure reported in Examples 9–11, with the only difference of introducing 100 mL hydrogen before adding propylene.

Polymerization data are reported in Table 1.

The obtained results confirm that the titanium complexes according to the present invention are sensitive to hydrogen as a molecular weight regulator.

EXAMPLE 14

Propylene/Ethylene Copolymerization

Propylene polymerization was carried out according to the procedure reported in Examples 9–11, with the only difference that, before charging the amount of propylene reported in Table 1, 4.1 g of ethylene were charged in the autoclave.

The resulting copolymer has an ethylene content of 0.8% wt ($^{13}C$ NMR), the other polymerization data, yields and characteristics of the obtained copolymer are reported in Table 1.

The obtained results demonstrate a good activity of the titanium complexes of the invention in propylene/ethylene copolymerization; the insertion of small amounts of ethylene in propylene polymers may serve to regulate the molecular weight of the final polymers, at the same time without negatively affecting intrinsic viscosity values and the yield of the process. The use of low amounts of ethylene in propylene polymerization process, according to the present invention, makes it possible to regulate the molecular weight of the obtained polymers.

EXAMPLE 15

Propylene Homopolymerization 1200 g of liquid propylene were loaded into a 4.25-L stainless-steel stirred reactor at 30° C., followed by 1 mmol of TIBA in hexane used as a scavenger. The temperature of the reactor was then raised up to 60° C.

The polymerization was started by injecting 2.1 mL of a toluene solution of MAO (ca. 6 mmol of Al) containing 1.4 mg of the B-3 into the autoclave at 60° C., by means of nitrogen overpressure, then the temperature was maintained at 60° C. for 37 min. The polymerization was stopped by venting and cooling the reactor.

The soft, non-sticky, amorphous product obtained was 530 g, corresponding to a yield of about 600 kg/($g_{cat}$×h). The properties of the polymer are:

I.V.=3.65 dL/g, no melting point (DSC), rr=72.16, rrrr= 51.7 ($^{13}C$ NMR).

Polymerization data, yields and characteristics of the obtained polymer are summarized in Table 1

EXAMPLE 16

Propylene Homopolymerization.

2 mL of a hexane solution of TIBA (1 mmol of TIBA in used as a scavenger), 271 g of liquid propylene were loaded into a 1-L stainless-steel stirred reactor at 30° C. The temperature of the reactor was then raised up to 70° C.

The polymerization was started by injecting 3 mL of a toluene solution of MAO (0.64 mmol of Al, MAO/Zr=500) containing 0.5 mg of B-3 into the autoclave at 70° C., by means of nitrogen overpressure, then the temperature was maintained at 70° C. for 60 min. The polymerization was stopped by pressurizing CO, venting and cooling the reactor.

The soft, non-sticky, amorphous product obtained was 53 g, corresponding to a yield of about 106 kg/($g_{cat}$×h). The properties of the polymer are:

I.V.=4.92 dL/g, no melting point (DSC).

Polymerization data, yields and characteristics of the obtained polymer are summarized in Table 1.

EXAMPLE 17

Propylene/Ethylene Copolymerization.

2 L of hexane were loaded into a 4.25-L stainless-steel stirred reactor at 30° C., followed by 2 mmol of TIBA in hexane used as a scavenger. 397 g of propylene and 38 g of ethylene were then pressurized into the reactor, and the temperature of the reactor was then raised up to 50° C., resulting in a pressure of 9.3 bar-g.

The polymerization was started by injecting 4.3 mL of a toluene solution containing MAO (1.29 mmol of Al) and 0.5 mg of B-3 into the autoclave at 50° C., by means of nitrogen overpressure, then the temperature was maintained at 50° C. and ethylene was continuously fed into the reactor in order to maintain a constant pressure. After 7 g of ethylene were added in 23 min, the polymerization was stopped by pressurizing 1.5 L of CO into the reactor, venting and cooling the reactor. The propylene/ethylene copolymer was recovered from the hexane solution by precipitation in acetone, followed by drying under reduced atmosphere at 70° C. for 4 hours.

104 g of non-sticky, amorphous copolymer were obtained, corresponding to a yield of about 540 kg/($g_{cat}$×h). The copolymer contains 20% by weight of ethylene ($^1H$ NMR analysis), is fully amorphous with $T_g$=−26° C., and has an intrinsic viscosity of 6.65 dL/g.

EXAMPLE 18

Propylene/Butene Copolymerization.

2 mL of a hexane solution of TIBA (1 mmol of TIBA in used as a scavenger), 158 g of propylene and 154 g of 1-butene were loaded into a 1-L stainless-steel stirred reactor at 30° C.

The temperature of the reactor was then raised up to 60° C. (15 bar-g).

The polymerization was started by injecting 3 mL of a toluene solution of MAO (ca. 2.6 mmol of Al) containing 1 mg of the B-3 into the autoclave at 60° C., by means of nitrogen overpressure, then the temperature was maintained at 60° C. for 60 min. The polymerization was stopped by pressurizing Co, venting and cooling the reactor.

The soft, non-sticky, amorphous product obtained was 13 g. The properties of the polymer are:

I.V.=0.9 dL/g, no melting point and $T_g$=−7° C., (DSC), butene=47 wt % (measured by $^{13}$C NMR).

EXAMPLE 19

Propylene/Butene Copolymerization

Example 18 was repeated at an Al/Zr ratio of 500, obtaining a copolymer with I.V.=2.11 dL/g.

EXAMPLE 20

Propylene Polymerizations at 80° C.

Following the usual procedure, 1 mmol of TIBA and 585 g of propylene were charged in a 2 L reactor, then heated to 80° C. 1 mg of B-3 was dissolved with 1.07 mL of a 10% MAO solution (1.82 mmol Al) in toluene and then diluted with toluene (total volume 3 mL), aged 10 min and injected into the reactor. The polymerization is stopped with CO after 60 min at 80° C. The results of polymer analysis are shown in Table 1.

EXAMPLE 21

Propylene Polymerizations at 80° C.

Following the usual procedure, 1 mmol of TIBA and 585 g of propylene were charged in a 2 L reactor, then heated to 80° C. 0.5 mg of B-3 was dissolved with 1.07 mL of a 10% MAO solution (1.82 mmol Al) in toluene and then diluted with toluene (total volume 3 mL), aged 10 min and injected into the reactor. The polymerization is stopped with CO after 60 min at 80° C. The results of polymer analysis are shown in Table 1.

EXAMPLES 22–23

Propylene polymerization was carried out according to the procedure reported in Examples 9–11, with the difference that B-4 was used as catalyst instead of B-1

Polymerization data, yields and characteristics of the obtained polymer are reported in Table 1.

EXAMPLES 24

Polymerization With Supported Catalysts 1200 g of liquid propylene were loaded into a 4.25-L stainless-steel stirred reactor at 30° C., followed by 1 mmol of TIBA in hexane used as a scavenger. 200 mL of hydrogen were added before the catalyst. 650 mg of the solid catalyst prepared in example 8 was then injected into the reactor by means of nitrogen overpressure through a stainless-steel vial, and then the temperature of the reactor was raised up to the polymerization temperature in 15 min.

After one hour, the polymerization was stopped by venting and cooling the reactor, and the amorphous product collected and dried.

Polymerization data, yields and characteristics of the obtained polymers are summarized in Table 1.

EXAMPLES 25

Propylene Polymerizations at 80° C.

Following the usual procedure, 1 mmol of TIBA and 585 g of propylene were charged in a 2 L reactor, then heated to 80° C. 1.5 mg of A-1 was dissolved with 1.07 mL of a 10% MAO solution (1.82 mmol Al) in toluene and then diluted with toluene (total volume 3 mL), aged 10 min and injected into the reactor. The polymerization is stopped with CO after 60 min at 80° C. 85 g of rubbery, amorphous polypropylene were recovered, corresponding to a catalyst activity of 56.6 $kg_{PP}/(g_{cat} \times h)$. The results of polymer analysis are shown in Table 1.

COMPARATIVE EXAMPLES 26–28

Propylene polymerization was carried out according to the procedure reported in Examples 9–11, with the difference that dimethylsilyl(tert-butylamido) (tetramethylcyclopentadienyl) titanium dichloride was used as catalyst instead of the titanium complex of the invention.

Polymerization data, yields and characteristics of the obtained polymer are reported in Table 1. The obtained result demonstrates that the titanium complexes of the invention are able to exert polymerization activities superior to the one of constrained geometry catalysts known in the state of the art.

COMPARATIVE EXAMPLE 29

Propylene polymerization was carried out according to the procedure reported in Example 9 with the difference that dimethylsilyl(tert-butylamido) (tetramethylcyclopentadienyl) titanium dichloride was used as catalyst instead of the titanium complex of the invention mixture. Polymerization data are reported in Table 1.

COMPARATIVE EXAMPLE 30

Propylene/ethylene copolymerization was carried out according to the procedure reported in Example 9 with the difference that 4.5 g of ethylene were added to the reactor before adding 288 g of propylene, dimethylsilyl(tert-butylamido)(tetramethylcyclopentadienyl) titanium dichloride (obtained by Witco) was used as catalyst instead of the titanium complex of the invention, and 15.7 g of ethylene were fed into the reactor over the polymerization time of 1 hour in order to maintain a constant pressure of 25.6 bar-g (of which 0.3 bar are due to nitrogen). The resulting copolymer has an ethylene content of 4.5% wt ($^{13}$C NMR), the other polymerization data are reported in Table 1.

COMPARATIVE EXAMPLES 31–32

Propylene polymerization was carried out according to the procedure reported in Examples 9–11, with the difference that dimethylsilyl(tert-butylamido)(indenyl) titanium dimethyl was used as catalyst instead of the titanium complex of the invention.

Polymerization data, yields and characteristics of the obtained polymer are reported in Table 1. The obtained result demonstrates that the titanium complexes of the invention are able to exert polymerization activities superior to the one of constrained geometry catalysts known in the state of the art.

COMPARATIVE EXAMPLE 33

Propylene polymerization was carried out according to the procedure reported in Examples 9–11, with the difference that dimethylsilyl(tert-butylamido)(2-methyl-indenyl) titanium dimethyl was used as catalyst instead of the titanium complex of the invention.

Polymerization data, yields and characteristics of the obtained polymer are reported in Table 1. The obtained result demonstrates that the titanium complexes of the invention are able to exert polymerization activities superior to the one of constrained geometry catalysts known in the state of the art.

TABLE 1

| Ex. | Ti complex | mg of complex | MAO/Ti Molar ratio | $T_{POL}$ °C | Time min | Activity $Kg_{PP}/g_{cat}$ | I.V. dL/g | tacticity (%) rr | rrrr | 2,1 |
|---|---|---|---|---|---|---|---|---|---|---|
| 9 | B-1 | 1 | 500 | 50 | 60 | 41.6 | 5.97 | 73.8 | 57.5 | <0.5 |
| 10 | B-1 | 1 | 1000 | 60 | 30 | 49.4 | 3.14 | 72.4 | 53.3 | <0.5 |
| 11 | B-1 | 0.7 | 1000 | 70 | 60 | 26.9 | 3.06 | 69.2 | 48.4 | <0.5 |
| 12 | B-1 | 1 | 500 | 70 | 60 | 37.9 | 4.69 | — | — | — |
| 13[a] | B-1 | 1 | 1000 | 60 | 60 | 12.2 | 1.84 | — | — | — |
| 14[b] | B-1 | 1 | 1000 | 60 | 30 | 81.7 | 2.41 | — | — | — |
| 15[c] | B-3 | 1.4 | 1000 | 60 | 37 | 530 | 3.65 | 72.2 | 51.7 | 0 |
| 16 | B-3 | 0.5 | 500 | 70 | 60 | 106 | 4.92 | — | — | — |
| 20 | B-3 | 1 | 500 | 80 | 60 | 288 | 4.16 | 68.9 | 48.1 | 0 |
| 21 | B-3 | 0.5 | 500 | 80 | 60 | 320 | 5.01 | 70.2 | 50.69 | 0 |
| 22 | B-4 | 0.3 | 1000 | 60 | 60 | 113 | 7.89 | 73.0 | 57.1 | 0.3 |
| 23 | B-4 | 0.5 | 1000 | 70 | 60 | 106 | 5.96 | 72.8 | 54.1 | 0 |
| 24[c] | B-4 | 610[f] | | 60 | 60 | 0.28[g] | 5.85 | — | — | — |
| 25 | A-1 | 1.5 | 500 | 80 | 60 | 56.7 | 4.25 | 33.4 | 10.6 | 0.5 |
| 26* | C-1[e] | 2 | 1000 | 60 | 60 | 29.5 | 3.56 | 50.2 | 25.3 | 1.3 |
| 27* | C-1[e] | 2 | 1000 | 70 | 60 | 31.5 | 2.58 | — | — | — |
| 28* | C-1[e] | 2 | 500 | 70 | 60 | 25.8 | 2.70 | — | — | — |
| 29*[a] | C-1[e] | 2 | 1000 | 60 | 60 | 23.8 | 2.42 | 52.1 | 25.4 | 1.5 |
| 30*[d] | C-1[e] | 2 | 1000 | 60 | 60 | 32.3 | 4.84 | — | — | — |
| 31* | C-3 | 2 | 1000 | 60 | 60 | 12.7 | 1.12 | — | — | — |
| 32* | C-3 | 2 | 500 | 70 | 60 | 7.1 | 0.92 | — | — | — |
| 33* | C-4 | 1 | 1000 | 60 | 60 | 18.3 | 3.15 | 51.4 | 28.3 | 0.6 |

[a] $H_2$ = 100 mL;
[b] $C_2^-$ = 4,1 g;
[c] 4.25 L reactor;
[d] $C_2^-$ = 17 g;
[e] dimethylsilyl(tertbutylamido)(tetramethylcyclopentadienyl) titanium dichloride (Witco);
[f] mg of supported catalyst;
[g] $Kg_{pol}/g_{support}$.
*comparative.

What is claimed is:

1. A process for producing substantially amorphous propylene homopolymers or copolymers comprising contacting propylene, optionally in the presence of one or more olefins selected from the group consisting of ethylene, alpha-olefins of formula $CH_2$=CHR' wherein R' is a linear or branched, $C_2$–$C_{10}$ alkyl or non conjugate diolefins containing up to 20 carbon atoms, under polymerization conditions with a catalyst system comprising:

A) a titanium complex of formula (I):

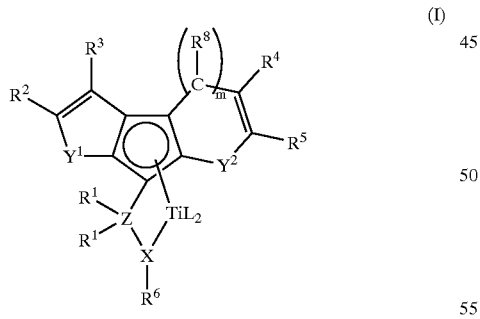

wherein: Ti is titanium;
X is a nitrogen (N) or phosphorus (P) atom;
Z is a C, Si or Ge atom;
the groups $R^1$, equal to or different from each other, are selected from the group consisting of hydrogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl optionally containing Si or heteroatoms belonging to groups 13 or 15–17 of the Periodic Table of the Elements, or two $R^1$ groups together form a $C_4$–$C_7$ ring;

$Y^1$ is an atom selected from the group consisting of $NR^7$, oxygen (O), $PR^7$ or sulfur (S), wherein the group $R^7$ is selected from the group consisting of linear or branched, saturated or unsaturated, $C_1$–$C_{20}$ alkyl, $C_6$–$C_{20}$ aryl and $C_7$–$C_{20}$ arylalkyl radicals;
the groups $R^2$ and $R^3$, equal to or different from each other, are selected from the group consisting of hydrogen, halogen, —R, —OR, —OCOR, —$OSO_2CF_3$, —SR, —$NR_2$ and —$PR_2$, wherein R is a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl radical; two R groups can also form a saturated or unsaturated $C_4$–$C_7$ ring, or $R^2$ and $R^3$ form a condensed aromatic or aliphatic $C_4$–$C_7$ ring that can be substituted with one or more $R^9$ groups, wherein $R^9$ is selected from the group consisting of halogen, —R, —OR, —OCOR, —$OSO_2CF_3$, —SR, —$NR_2$ and —$PR_2$, wherein R has the meaning reported above, or two vicinal $R^9$ groups together form a condensed aromatic or aliphatic $C_4$–$C_7$ ring;
the groups $R^8$, $R^4$ and $R^5$, equal to or different from each other, are selected from the group consisting of hydrogen, halogen, —R, —OR, —OCOR, —$OSO_2CF_3$, —SR, —$NR_2$ and —$PR_2$, wherein R has the meaning reported above, or $R^8$ and $R^4$, $R^4$ and $R^5$, or $R^5$ and $R^8$ together form a condensed $C_4$–$C_7$ ring that can be substituted with one or more R groups;
the group $R^6$ is selected from the group consisting of a linear or branched, saturated or unsaturated $C_1$–$C_{20}$ alkyl, $C_6$–$C_{20}$ aryl and $C_7$–$C_{20}$ arylalkyl radical, optionally containing heteroatoms belonging to groups 13 or 15–17 of the Periodic Table of the Elements;

the substituents L, equal to or different from each other, are monoanionic sigma ligands selected from the group consisting of hydrogen, halogen, —R, —OR, —OCOR, —OSO$_2$CF$_3$, —SR, —NR$_2$ and —PR$_2$, wherein R has the meaning reported above;

$Y^2$ is selected from the group consisting of CR$^8$ or $Y^1$; and m is 0 or 1; when the group $Y^2$ is a CR$^8$ group m is 1 and the 6 membered ring formed is an aromatic benzene ring; when $Y^2$ is different from CR$^8$ m is 0 and the carbon atom bonding the R$^4$ group is directly bonded to the cyclopentadienyl ring and the ring formed is a 5 membered ring; and (B) an activating cocatalyst.

2. The process according to claim 1 wherein the titanium complex has formula (III)

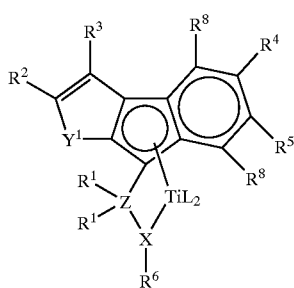
(III)

wherein X, Z, $Y^1$, L, $R^1$, $R^2$, $R^3$, $R^4$, $R^5$, $R^6$ and $R^8$ have the meaning reported in claim 1 with the proviso that $R^2$ and $R^3$ do not form a condensed aromatic C$_6$ ring.

3. The process according to claim 2 wherein in the titanium complex of formula (III):

X is a nitrogen atom; the divalent bridge >ZR$^1{}_2$ is selected from the group consisting of dimethylsilyl, diphenylsilyl, diethylsilyl, di-n-propylsilyl, di-isopropylsilyl, di-n-butyl-silyl, di-t-butyl-silyl, di-n-hexylsilyl, ethylmethylsilyl, n-hexylmethylsilyl, cyclopentamethylenesilyl, cyclotetramethylenesilyl, cyclotrimethylenesilyl, methylene, dimethylmethylene and diethylmethylene;

$Y^1$ is N-methyl, N-ethyl or N-phenyl;

$R^2$ is hydrogen, methyl, ethyl, propyl or phenyl;

$R^3$ is hydrogen methyl or phenyl;

$R^4$ and $R^8$ are hydrogen, methyl;

$R^5$ is hydrogen, methoxy or tert-butyl;

$R^6$ is selected from the group consisting of methyl, ethyl, n-propyl, isopropyl, n-butyl, t-butyl, phenyl, p-n-butyl-phenyl, benzyl, cyclohexyl and cyclododecyl;

the substituents L, equal to or different from each other, are preferably halogen atoms, linear or branched, saturated or unsaturated C$_7$–C$_{20}$ alkylaryl, C$_1$–C$_6$ alkyl groups or OR wherein R is a linear or branched, saturated or unsaturated C$_1$–C$_{20}$ alkyl, C$_3$–C$_{20}$ cycloalkyl, C$_6$–C$_{20}$ aryl, C$_7$–C$_{20}$ alkylaryl or C$_7$–C$_{20}$ arylalkyl radical; and two R groups can also form a saturated or unsaturated C$_4$–C$_7$ ring.

4. The process according to claim 1 wherein the titanium complex has formula (IV)

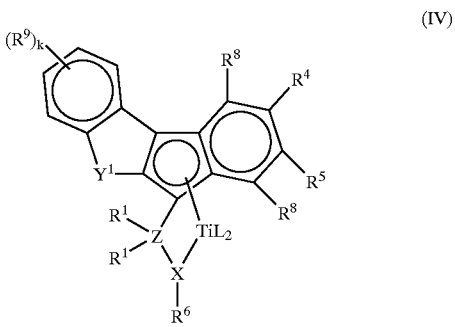
(IV)

wherein X, Z, $Y^1$, L, $R^1$, $R^5$, $R^6$, $R^8$, and $R^9$ have the meaning reported in claim 1 and k ranges from 0 to 4.

5. The process according to claim 4 wherein in the titanium complex of formula (IV):

X is a nitrogen atom; the divalent bridge >ZR$^1{}_2$ is selected from the group consisting of dimethylsilyl, diphenylsilyl, diethylsilyl, di-n-propylsilyl, di-isopropylsilyl, di-n-butyl-silyl, di-t-butyl-silyl, di-n-hexylsilyl, ethylmethylsilyl, n-hexylmethylsilyl, cyclopentamethylenesilyl, cyclotetramethylenesilyl, cyclotrimethylenesilyl, methylene, dimethylmethylene and diethylmethylene;

$Y^1$ is N-methyl, N-ethyl or N-phenyl;

k is 0 or 1 and $R^9$ is 2-methyl, 2-tert-butyl, 2-methoxy;

$R^6$ is selected from the group consisting of methyl, ethyl, n-propyl, isopropyl, n-butyl, t-butyl, phenyl, p-n-butyl-phenyl, benzyl, cyclohexyl and cyclododecyl;

$R^4$, $R^5$ and $R^8$ are hydrogen atoms;

the substituents L, equal to or different from each other, are halogen atoms, linear or branched, saturated or unsaturated C$_1$–C$_6$ alkyl, C$_7$–C$_{20}$ alkylaryl groups or OR wherein R is a linear or branched, saturated or unsaturated C$_1$–C$_{20}$ alkyl, C$_3$–C$_{20}$ cycloalkyl, C$_6$–C$_{20}$ aryl, C$_7$–C$_{20}$ alkylaryl or C$_7$–C$_{20}$ arylalkyl radical; and two R groups can also form a saturated or unsaturated C$_4$–C$_7$ ring.

6. The process according to claim 1 wherein the titanium complex has formula (V)

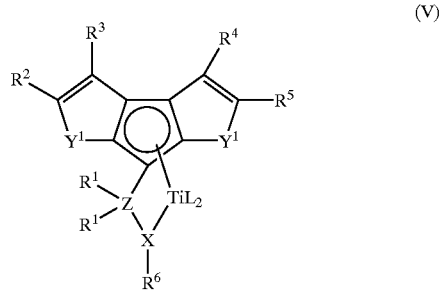
(V)

wherein X, Z, L, $Y^1$, $R^1$, $R^2$, $R^3$, $R^4$, $R^5$ and $R^6$ have the meaning reported in claim 1.

7. The process according to claim 6 wherein in the titanium complex of formula (V):

X is a nitrogen atom; the divalent bridge >ZR$^1{}_2$ is preferably selected from the group consisting of dimethylsilyl, diphenylsilyl, diethylsilyl, di-n-propylsilyl, di-isopropylsilyl, di-n-butyl-silyl, di-t-butyl-silyl, di-n-hexylsilyl, ethylmethylsilyl, n-hexylmethylsilyl, cyclopentamethylenesilyl, cyclotetramethylenesilyl, cyclotrimethylenesilyl, methylene, dimethylmethylene and diethylmethylene;

two $Y^1$ are the same group;

$R^2$ is hydrogen, methyl, ethyl, propyl or phenyl; and $R^4$ is hydrogen or $R^2$ and $R^3$ form a condensed benzene ring that can be substituted with one or more R groups;

$R^4$ is hydrogen and $R^5$ is hydrogen, methyl, ethyl, propyl or phenyl or $R^4$ and $R^5$ form a condensed benzene ring that can be substituted with one or more R groups;

$R^6$ is selected from the group consisting of methyl, ethyl, n-propyl, isopropyl, n-butyl, t-butyl, phenyl, p-n-butyl-phenyl, benzyl, cyclohexyl and cyclododecyl;

the substituents L, equal to or different from each other, are preferably halogen atoms, linear or branched, saturated or unsaturated $C_7$–$C_{20}$ alkylaryl, $C_1$–$C_6$ alkyl groups or OR wherein R is a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl radical; and two R groups can also form a saturated or unsaturated $C_4$–$C_7$ ring.

8. The process according to claim 1 wherein the cocatalyst is selected from the group consisting of alumoxanes or compounds capable of forming an alkyl metallocene cation.

9. The process according to claim 1 wherein the catalyst system is supported on an inert carrier.

10. The process according to claim 9 wherein the inert carrier is selected from the group consisting of silica, alumina, magnesium halides, olefin polymers or prepolymers.

11. The process according to claim 9 wherein the catalyst system is supported by depositing a component selected from the group consisting of (a) the titanium complex (A), (b) the reaction product of the titanium complex (A) with the cocatalyst B), and (c) the cocatalyst (B) and subsequently the titanium complex (A), on an inert support.

12. The process according to claim 1 wherein the process is carried out in gaseous phase.

13. A titanium complex of formula (I):

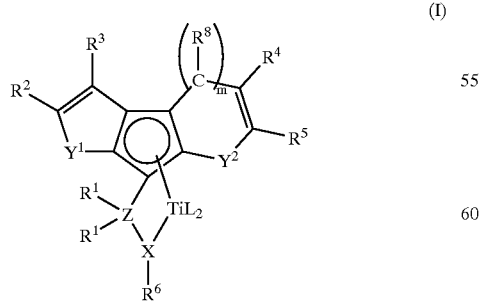

(I)

wherein X, Z, L, $Y^1$, $Y^2$, m, $R^1$, $R^2$, $R^3$, $R^4$, $R^5$, $R^6$ and $R^8$ have the meaning reported in claim 1.

14. The titanium complex according to claim 13 having formula (III):

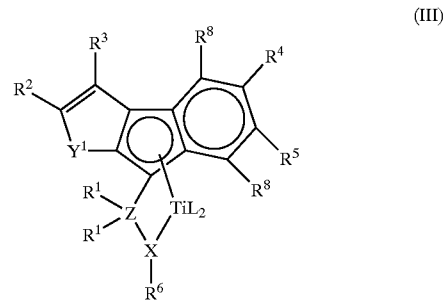

(III)

wherein X is a nitrogen (N) or phosphorus (P) atom;

Z is a C, Si or Ge atom;

the groups $R^1$, equal to or different from each other, are selected from the group consisting of hydrogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl optionally containing Si or heteroatoms belonging to groups 13 or 15–17 of the Periodic Table of the Elements, or two $R^1$ groups together form a $C_4$–$C_7$ ring;

$Y^1$ is an atom selected from the group consisting of $NR^7$, oxygen (O), $PR^7$ or sulfur (S), wherein the group $R^7$ is selected from the group consisting of linear or branched, saturated or unsaturated, $C_1$–$C_{20}$ alkyl, $C_6$–$C_{20}$ aryl and $C_7$–$C_{20}$ arylalkyl radicals;

the groups $R^2$ and $R^3$, equal to or different from each other, are selected from the group consisting of hydrogen, halogen, —R, —OR, —OCOR, —OSO$_2$CF$_3$, —SR, —NR$_2$ and —PR$_2$, wherein R is a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl radical; two R groups can also form a saturated or unsaturated $C_4$–$C_7$ ring, or $R^2$ and $R^3$ form a condensed aromatic or aliphatic $C_4$–$C_7$ ring that can be substituted with one or more $R^9$ groups, wherein $R^9$ is selected from the group consisting of halogen, —R, —OR, —OCOR, —OSO$_2$CF$_3$, —SR, —NR$_2$ and —PR$_2$, wherein R has the meaning reported above, or two vicinal $R^9$ groups together form a condensed aromatic or aliphatic $C_4$–$C_7$ ring;

the groups $R^8$, $R^4$ and $R^5$, equal to or different from each other, are selected from the group consisting of hydrogen, halogen, —R, —OR, —OCOR, —OSO$_2$CF$_3$, —SR, —NR$_2$ and —PR$_2$, wherein R has the meaning reported above, or $R^8$ and $R^4$, $R^4$ and $R^5$, or $R^5$ and $R^8$ together form a condensed $C_4$–$C_7$ ring that can be substituted with one or more R groups;

the group $R^6$ is selected from the group consisting of a linear or branched, saturated or unsaturated $C_1$–$C_{20}$ alkyl, $C_6$–$C_{20}$ aryl and $C_7$–$C_{20}$ arylalkyl radical, optionally containing heteroatoms belonging to groups 13 or 15–17 of the Periodic Table of the Elements; and the substituents L, equal to or different from each other, are monoanionic sigma ligands selected from the group consisting of hydrogen, halogen, —R, —OR, —OCOR, —OSO$_2$CF$_3$, —SR, —NR$_2$ and —PR$_2$, wherein R has the meaning reported above;

with the proviso that $R^2$ and $R^3$ do not form a condensed aromatic $C_6$ ring.

15. The titanium complex according to claim 13 having formula (IV):

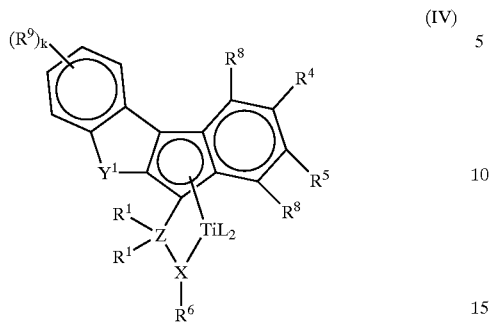

wherein X is a nitrogen (N) or phosphorus (P) atom;

Z is a C, Si or Ge atom;

the groups $R^1$, equal to or different from each other, are selected from the group consisting of hydrogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl optionally containing Si or heteroatoms belonging to groups 13 or 15–17 of the Periodic Table of the Elements, or two $R^1$ groups together form a $C_4$–$C_7$ ring;

$Y^1$ is an atom selected from the group consisting of $NR^7$, oxygen (O), $PR^7$ or sulfur (S), wherein the group $R^7$ is selected from the group consisting of linear or branched, saturated or unsaturated, $C_1$–$C_{20}$ alkyl, $C_6$–$C_{20}$ aryl and $C_7$–$C_{20}$ arylalkyl radicals;

$R^9$ is selected from the group consisting of halogen, —R, —OR, —OCOR, —OSO$_2$CF$_3$, —SR, —NR$_2$ and —PR$_2$, wherein R is a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl radical; and two R groups can also form a saturated or unsaturated $C_4$–$C_7$ ring, or two vicinal $R^9$ groups together form a condensed aromatic or aliphatic $C_4$–$C_7$ ring;

the groups $R^8$, $R^4$ and $R^5$, equal to or different from each other, are selected from the group consisting of hydrogen, halogen, —R, —OR, —OCOR, —OSO$_2$CF$_3$, —SR, —NR$_2$ and —PR$_2$, wherein R has the meaning reported above, or $R^8$ and $R^4$, $R^4$ and $R^5$, or $R^5$ and $R^8$ together form a condensed $C_4$–$C_7$ ring that can be substituted with one or more R groups;

the group $R^6$ is selected from the group consisting of a linear or branched, saturated or unsaturated $C_1$–$C_{20}$ alkyl, $C_6$–$C_{20}$ aryl and $C_7$–$C_{20}$ arylalkyl radical, optionally containing heteroatoms belonging to groups 13 or 15–17 of the Periodic Table of the Elements;

the substituents L, equal to or different from each other, are monoanionic sigma ligands selected from the group consisting of hydrogen, halogen, —R, —OR, —OCOR, —OSO$_2$CF$_3$, —SR, —NR$_2$ and —PR$_2$, wherein R has the meaning reported above;

and k ranges from 0 to 4.

16. The titanium complex according to claim 13 having formula (V):

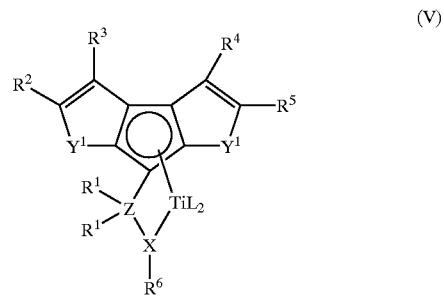

wherein: X is a nitrogen (N) or phosphorus (P) atom;

Z is a C, Si or Ge atom;

the groups $R^1$, equal to or different from each other, are selected from the group consisting of hydrogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl optionally containing Si or heteroatoms belonging to groups 13 or 15–17 of the Periodic Table of the Elements, or two $R^1$ groups together form a $C_4$–$C_7$ ring;

$Y^1$ is an atom selected from the group consisting of $NR^7$, oxygen (O), $PR^7$ or sulfur (S), wherein the group $R^7$ is selected from the group consisting of linear or branched, saturated or unsaturated, $C_1$–$C_{20}$ alkyl, $C_6$–$C_{20}$ aryl and $C_7$–$C_{20}$ arylalkyl radicals;

the groups $R^2$ and $R^3$, equal to or different from each other, are selected from the group consisting of hydrogen, halogen, —R, —OR, —OCOR, —OSO$_2$CF$_3$, —SR, —NR$_2$ and —PR$_2$, wherein R is a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl radical; two R groups can also form a saturated or unsaturated $C_4$–$C_7$ ring, or $R^2$ and $R^3$ form a condensed aromatic or aliphatic $C_4$–$C_7$ ring that can be substituted with one or more $R^9$ groups, wherein $R^9$ is selected from the group consisting of halogen, —R, —OR, —OCOR, —OSO$_2$CF$_3$, —SR, —NR$_2$ and —PR$_2$, wherein R has the meaning reported above, or two vicinal $R^9$ groups together form a condensed aromatic or aliphatic $C_4$–$C_7$ ring;

the groups $R^4$ and $R^5$, equal to or different from each other, are selected from the group consisting of hydrogen, halogen, —R, —OR, —OCOR, —OSO$_2$CF$_3$, —SR, —NR$_2$ and —PR$_2$, wherein R has the meaning reported above, or $R^4$ and $R^5$ together form a condensed $C_4$–$C_7$ ring that can be substituted with one or more R groups;

the group $R^6$ is selected from the group consisting of a linear or branched, saturated or unsaturated $C_1$–$C_{20}$ alkyl, $C_6$–$C_{20}$ aryl and $C_7$–$C_{20}$ arylalkyl radical, optionally containing heteroatoms belonging to groups 13 or 15–17 of the Periodic Table of the Elements; and the substituents L, equal to or different from each other, are monoanionic sigma ligands selected from the group consisting of hydrogen, halogen, —R, —OR, —OCOR, —OSO$_2$CF$_3$, —SR, —NR$_2$ and —PR$_2$, wherein R has the meaning reported above.

17. A ligand of formula (II):

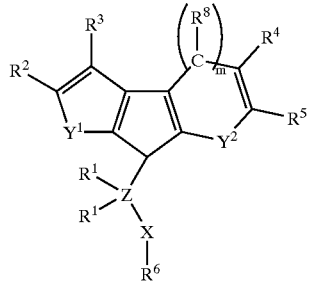

(II)

wherein X, Z, m, $Y^1$, $Y^2$, $R^1$, $R^2$, $R^3$, $R^4$, $R^5$, $R^6$, and $R^8$ have the meaning reported in claim 1.

18. The ligand according to claim 17 having formula (IIIa):

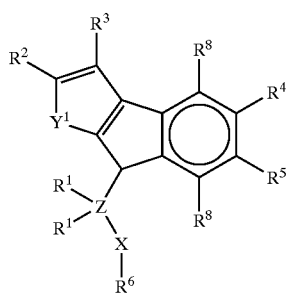

(IIIa)

wherein X is a nitrogen (N) or phosphorus (P) atom;

Z is a C, Si or Ge atom;

the groups $R^1$, equal to or different from each other, are selected from the group consisting of hydrogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl optionally containing Si or heteroatoms belonging to groups 13 or 15–17 of the Periodic Table of the Elements, or two $R^1$ groups together form a $C_4$–$C_7$ ring;

$Y^1$ is an atom selected from the group consisting of $NR^7$, oxygen (O), $PR^7$ or sulfur (S), wherein the group $R^7$ is selected from the group consisting of linear or branched, saturated or unsaturated, $C_1$–$C_{20}$ alkyl, $C_6$–$C_{20}$ aryl and $C_7$–$C_{20}$ arylalkyl radicals;

the groups $R^2$ and $R^3$, equal to or different from each other, are selected from the group consisting of hydrogen, halogen, —R, —OR, —OCOR, —OSO$_2$CF$_3$, —SR, —NR$_2$ and —PR$_2$, wherein R is a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl radical; two R groups can also form a saturated or unsaturated $C_4$–$C_7$ ring, or $R^2$ and $R^3$ form a condensed aromatic or aliphatic $C_4$–$C_7$ ring that can be substituted with one or more $R^9$ groups, wherein $R^9$ is selected from the group consisting of halogen, —R, —OR, —OCOR, —OSO$_2$CF$_3$, —SR, —NR$_2$ and —PR$_2$, wherein R has the meaning reported above, or two vicinal $R^9$ groups together form a condensed aromatic or aliphatic $C_4$–$C_7$ ring;

the groups $R^8$, $R^4$ and $R^5$, equal to or different from each other, are selected from the group consisting of hydrogen, halogen, —R, —OR, —OCOR, —OSO$_2$CF$_3$, —SR, —NR$_2$ and —PR$_2$, wherein R has the meaning reported above, or $R^8$ and $R^4$, $R^4$ and $R^5$, or $R^5$ and $R^8$ together form a condensed $C_4$–$C_7$ ring that can be substituted with one or more R groups; and the group $R^6$ is selected from the group consisting of a linear or branched, saturated or unsaturated $C_1$–$C_{20}$ alkyl, $C_6$–$C_{20}$ aryl and $C_7$–$C_{20}$ arylalkyl radical, optionally containing heteroatoms belonging to groups 13 or 15–17 of the Periodic Table of the Elements;

with the proviso that $R^2$ and $R^3$ do not form a condensed aromatic $C_6$ ring.

19. The ligand according to claim 17 having formula (IVa):

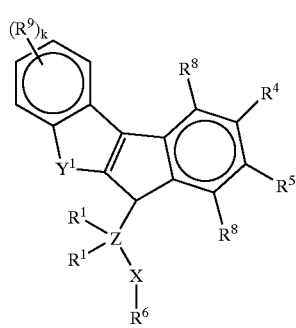

(IVa)

wherein X is a nitrogen (N) or phosphorus (P) atom;

Z is a C, Si or Ge atom;

the groups $R^1$, equal to or different from each other, are selected from the group consisting of hydrogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl optionally containing Si or heteroatoms belonging to groups 13 or 15–17 of the Periodic Table of the Elements, or two $R^1$ groups together form a $C_4$–$C_7$ ring;

$Y^1$ is an atom selected from the group consisting of $NR^7$, oxygen (O), $PR^7$ or sulfur (S), wherein the group $R^7$ is selected from the group consisting of linear or branched, saturated or unsaturated, $C_1$–$C_{20}$ alkyl, $C_6$–$C_{20}$ aryl and $C_7$–$C_{20}$ arylalkyl radicals;

$R^9$ is selected from the group consisting of halogen, —R, —OR, —OCOR, —OSO$_2$CF$_3$, —SR, —NR$_2$ and —PR$_2$, wherein R is linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl radical; two R groups can also form a saturated or unsaturated $C_4$–$C_7$ ring, or two vicinal $R^9$ groups together form a condensed aromatic or aliphatic $C_4$–$C_7$ ring;

the groups $R^8$, $R^4$ and $R^5$, equal to or different from each other, are selected from the group consisting of hydrogen, halogen, —R, —OR, —OCOR, —OSO$_2$CF$_3$, —SR, —NR$_2$ and —PR$_2$, wherein R has the meaning reported above, or $R^8$ and $R^4$, $R^4$ and $R^5$, or $R^5$ and $R^8$ together form a condensed $C_4$–$C_7$ ring that can be substituted with one or more R groups;

the group $R^6$ is selected from the group consisting of a linear or branched, saturated or unsaturated $C_1$–$C_{20}$ alkyl, $C_6$–$C_{20}$ aryl and $C_7$–$C_{20}$ arylalkyl radical, optionally containing heteroatoms belonging to groups 13 or 15–17 of the Periodic Table of the Elements;

and k ranges from 0 to 4.

20. The ligand according to claim 17 having formula (Va):

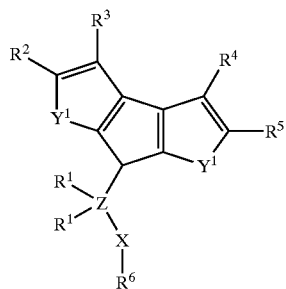

(Va)

wherein X is a nitrogen (N) or phosphorus (P) atom;

Z is a C, Si or Ge atom;

the groups $R^1$, equal to or different from each other, are selected from the group consisting of hydrogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl optionally containing Si or heteroatoms belonging to groups 13 or 15–17 of the Periodic Table of the Elements, or two $R^1$ groups together form a $C_4$–$C_7$ ring;

$Y^1$ is an atom selected from the group consisting of $NR^7$, oxygen (O), $PR^7$ or sulfur (S), wherein the group $R^7$ is selected from the group consisting of linear or branched, saturated or unsaturated, $C_1$–$C_{20}$ alkyl, $C_6$–$C_{20}$ aryl and $C_7$–$C_{20}$ arylalkyl radicals;

the groups $R^2$ and $R^3$, equal to or different from each other, are selected from the group consisting of hydrogen, halogen, —R, —OR, —OCOR, —OSO$_2$CF$_3$, —SR, —NR$_2$ and —PR$_2$, wherein R is a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl radical; two R groups can also form a saturated or unsaturated $C_4$–$C_7$ ring, or $R^2$ and $R^3$ form a condensed aromatic or aliphatic $C_4$–$C_7$ ring that can be substituted with one or more $R^9$ groups, wherein $R^9$ is selected from the group consisting of halogen, —R, —OR, —OCOR, —OSO$_2$CF$_3$, —SR, —NR$_2$ and —PR$_2$, wherein R has the meaning reported above, or two vicinal $R^9$ groups together form a condensed aromatic or aliphatic $C_4$–C—, ring;

the groups $R^4$ and $R^5$, equal to or different from each other, are selected from the group consisting of hydrogen, halogen, —R, —OR, —OCOR, —OSO$_2$CF$_3$, —SR, —NR$_2$ and —PR$_2$, wherein R has the meaning reported above or $R^4$ and $R^5$ together form a condensed $C_4$–$C_7$ ring that can be substituted with one or more R groups; and the group $R^6$ is selected from the group consisting of a linear or branched, saturated or unsaturated $C_1$–$C_{20}$ alkyl, $C_6$–$C_{20}$ aryl and $C_7$–$C_{20}$ arylalkyl radical, optionally containing heteroatoms belonging to groups 13 or 15–17 of the Periodic Table of the Elements.

21. A process for preparing the ligand of formula (II)

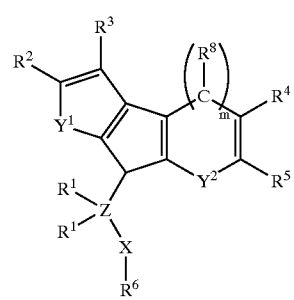

(II)

wherein X, Z, m, $Y^1$, $Y^2$, $R^1$, $R^2$, $R^3$, $R^4$, $R^5$, $R^6$, and $R^8$ have the meaning reported in claim 1, comprising the following steps, i) reacting a compound of formula (VI):

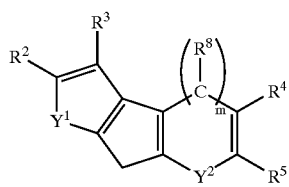

(VI)

wherein $Y^1$, m, $R^2$, $R^3$, $R^4$, $R^5$, and $R^8$ have the meaning reported above, with at least one equivalent of a base and then contacting the obtained compound with a compound of formula $R^1{}_2ZY^3Y^4$, wherein $R^1$ and Z have the meaning reported in claim 1, $Y^3$ is a halogen atom and $Y^4$ is an halogen atom or a group $R^6$XH wherein $R^6$ and X have the meaning reported in claim 1 and H is hydrogen;

ii) if $Y^4$ is an halogen atom, reacting the obtained product with a compound of formula $R^6XH_2$ wherein $R^6$ and X have the meaning reported in claim 1 and H is hydrogen, and recovering the product.

22. A process for preparing the titanium complexes of formula (I) as described in claim 1 comprising: reacting a ligand of formula (II)

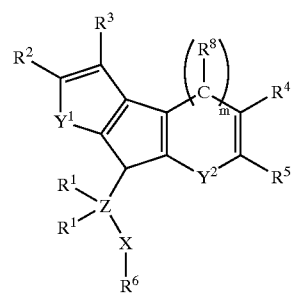

(II)

wherein X, Z, m, $Y^1$, $Y^2$, $R^1$, $R^2$, $R^3$, $R^4$, $R^5$, $R^6$, and $R^8$ have the meaning reported in claim 1, with a compound able to form a delocalized dianion on the cyclopentadienyl ring and on the group X as described in claim 1, and thereafter with a compound of formula TiL'$_4$, wherein the substituents L' are halogen or —OR, wherein R has the meaning reported in claim 1.

* * * * *

UNITED STATES PATENT AND TRADEMARK OFFICE
CERTIFICATE OF CORRECTION

PATENT NO. : 6,730,754 B2
DATED : May 4, 2004
INVENTOR(S) : Luigi Resconi et al.

Page 1 of 1

It is certified that error appears in the above-identified patent and that said Letters Patent is hereby corrected as shown below:

Column 38,
Line 16, after "$R^1$," insert -- $R^4$, --.

Column 45,
Line 53, change "$C_4$-C-," to -- $C_4$-$C_7$, --.

Signed and Sealed this

Fifteenth Day of November, 2005

JON W. DUDAS
*Director of the United States Patent and Trademark Office*